United States Patent [19]

Stocco et al.

[11] Patent Number: 5,872,230
[45] Date of Patent: Feb. 16, 1999

[54] COMPOSITIONS AND METHODS FOR REGULATION OF STEROIDOGENESIS

[75] Inventors: Douglas M. Stocco, Lubbock, Tex.; Barbara J. Clark, Louisville, Ky.

[73] Assignee: Texas Tech University Health Sciences Center, Lubbock, Tex.

[21] Appl. No.: 538,960

[22] Filed: Nov. 4, 1995

[51] Int. Cl.$^6$ .............................. C07H 21/00; C12Q 1/68
[52] U.S. Cl. .......................... 536/22.1; 435/6; 536/23.1; 536/23.5
[58] Field of Search ................................ 435/6; 536/22.1, 536/23.1, 23.5

[56] References Cited

PUBLICATIONS

Clark, et al., "The Purification, Cloning, and Expression of a Novel Luteinizing Hormone–induced Mitochondrial Protein in MA–10 Mouse Leydig Tumor Cells", *The Journal of Biological Chemistry*, vol. 269, no. 45, Nov. 11, 1994, pp. 28314–28322.

Lin, et al., "The Role of Steroidogenic Acute Regulatory Protein in Adrenal and Gonadal Steroidogenesis", *Science*, vol. 267, pp. 1828–1831, Mar. 24, 1995.

Sugawara, et al., "Structure of the Human Steroidogenic Acute Regulatory Protein (StAR) Gene: StAR Stimulates Mitochondrial Cholesterol 27–Hydroxylase Activity", *Biochemistry* (1995), 34:12506–12512.

Clark, et al., "Expression of the Steroidogenic Acute Regulatory (StAR) Protein: A Novel LH–Induced Mitochondrial Protein Required for the Acute Regulation of Steroidogenesis in Mouse Leydig Tumor Cells", *Endocrine Research*, 21 (1&2), 243–257 (1995).

Clark, et al., "Hormonal and Development Regulation of the Steroidogenic Acute Regulatory Protein", *Molecular Endocrinology*, vol. 9, No. 10, 1346–1355 (1995).

King, et al., "Steroid Production after in Vitro Transcription, Translation, and Mitochondrial Processing of Protein Products of Complementary Deoxyribonucleic Acid for Steroidogenic Acute Regulatory Protein", *Endocrinology*, vol. 136, No. 11, 5165–5176 (1995).

Stocco, et al., "Characterization of the Protein Responsible for the Acute Regulation of Steroidgenesis in Mouse Leydig Tumor Cells", XIII$^{th}$ Testis Workshop: Cellular and Molecular Regulation of Testicular Cells, Final Program and Abstract Book, Mar. 30–Apr. 1, 1995, Raleigh North Carolina, Serono Symposia USA.

Clark, Barbara J. and Stocco, Douglas M., "Expression of a Novel LH–Induced Protein Responsible for the Acute Regulation of Steroidogenesis in Mouse Leydig Tumor Cells", Dallas IX International Congress on Hormonal Steroids, Sep. 24–29, 1994, Hyatt Regency at Reunion, Dallas, Texas, C185;.

Huang, et al., "Corticotropin–Releasing Hormone (CRH) Stimulates Steroidogensis in Mouse Leydig Cells", Society for the Study of Reproduction, Biology of Reproduction/vol. 50/Supplement 1, Jul. 24–27, 1994, 27th Annual Meeting, University of Michigan, Ann Arbor, Michigan.

Keyes, et al., "Steroidogenic Acute Regulatory Protein (StAR) in the Rabbit Corpus Luteum: Dependence Upon the Luteotropic Hormone, 17β–Estradiol", Society for the Study of Reproduction, Biology of Reproduction/vol. 52/Supplement 1, 39, Jul. 9–12, 1995, 28th Annual Meeting, University of Michigan, Ann Arbor, Michigan.

Lin, D., et al., "Mutations in Steroidogenic Acute Regulatory Protein (StAR) Cause Congenital lipoid Adrenal Hyperplasia (Lipoid CAH) : Genetic Evidence for an Indispensible Role for StAR in Adrenal and Gonadal Steroidogeneisi", Program & Abstracts, P3–620, 77th Annual Meeting, Jun. 14–17, 1995, Washington, D.C.

Lipid Metabolism 1995, Kimball Union Academy, Meriden, NH, Jun. 25–30.

Ronen–Fuhrmann, et al., "Steroidogenic Acute Regulatory Protein (StAR) : Immunocytochemical Characterization of a Novel Hormone–Induced Protein Required for the Acute Regulation of Steroidogenesis", Israel Endocrine Society, 1995.

Conference on the Adrenal Cortex, 1994.

Gradi et al. "The human stereoidogenic acute regulatory (StAR) gene is expressed inthe urogenital system and encodes a mitochondrial polypeptide" Biochimica et Biophysica Acta, 1258, pp. 228–233, 1995.

Wistow et al. "Gene conversion and splice–site slippage in the argininosuccinate lyases/–crystallins ofthe duck lens: members of an enzyme superfamily" Gene, 96, pp. 263–270, 1990.

Willekens et al. "Molecular identification of catalases from *Nicotiana plumbaginifolia* (L.)" FEBS Letters, 252, pp. 79–83, 1994.

Sugawara et al. "Human stereoidogenic acute regulatory protein: functional activity in COS–1 cells, tissu–specific expression, and mapping of the dtructural gene to 8p11.2 and a pseudogene to chromosone 13" Proc. Natl. Acad. Sci. USA, 92, pp. 4778–4782, 1995.

Sorensen et al. Barley (*Hordeum vulgare*) gene for CP29, a core chlorophyll a/b binding protein of photosystem II Plant Physiology, 98, pp. 1538–1540, 1992.

Matsuoka et al. "Isolation, hyperexpression, and sequencing of the aceA gene encoding isocitrate lyase in *Escherichia coli*" Journal of Bacteriology, vol. 170, No. 10, pp. 4528–4536, 1988.

*Primary Examiner*—Ardin H. Marschel
*Assistant Examiner*—Jezia Riley
*Attorney, Agent, or Firm*—Locke Purnell Rain Harrell; Denise Mayfield

[57] ABSTRACT

Compositions and methods relating to the regulation of transport of cholesterol into the mitochondria of a cell and, therefore, for the regulation of steroidogenesis are provided. Compositions include nucleic acid molecules encoding a steroidogenic acute regulatory protein (StAR), StAR protein molecules and peptides having amino acid sequences as disclosed herein, and anti-StAR antibodies. Methods include immunoassays using anti-StAR antibodies and nucleic acid based screening methods for pathologies correlated with defects in StAR, such as lipoid congenital adrenal hyperplasia. In addition, these compositions and methods may be useful for treatment of steroid hormone-dependent disorders, in particular, for lipoid congenital adrenal hyperplasia.

19 Claims, No Drawings

COMPOSITIONS AND METHODS FOR REGULATION OF STEROIDOGENESIS

The government owns certain rights in the present invention pursuant to grant numbers HD17481 and HD07688 from the National Institutes of Health.

FIELD OF THE INVENTION

The present invention relates generally to compositions and methods for the regulation of steroidogenesis. More particularly, it concerns compositions and methods relating to the regulation of transport of cholesterol into the mitochondria of a cell for the synthesis of androgens, estrogens, glucocorticoids, mineralocorticoids, and progestagens. The invention also relates to methods for detecting and treating steroid hormone-dependent disorders. The nucleic acid molecules of the present invention also provide methods for screening a sample for steroid hormone-dependent disorders. The invention also relates to the field of nucleic acid probes and primers, as the various nucleic acid molecules of the invention may be used as molecular probes in all of the aforedescribed methods, as well as primers for amplifying particular sequences of interest.

BACKGROUND OF THE INVENTION

The testis is known to be the source of circulating androgens that are responsible for the maintenance of the secondary sexual characteristics in the male. In most species the testis has two separate compartments: the seminiferous tubules that contain the Sertoli cells, the peritubular cells, and the germ cells; and the interstitial compartment that contains the Leydig cells, macrophages, lymphocytes, granulocytes and the cells composing the blood, nerve and lymphatic structures.

The Leydig cells, located in the interstitial compartment and comprising approximately 2–3% of the total testicular cell number in most species, are the only cells in the testis that contain two key steroidogenic enzymes, namely, cytochrome P450 side chain cleavage (P450scc) and 3 beta-hydroxysteroid dehydrogenase (3 beta-HSD). Thus, Leydig cells are the only testicular cells capable of the first two steps in steroidogenesis; i) the conversion of cholesterol, the substrate for all steroid hormones, to pregnenolone; and ii) conversion of pregnenolone to progesterone. Therefore, the interstitial compartment in general, and the Leydig cells in particular synthesize virtually all of the steroids produced in the testis, with testosterone being the major steroid biosynthesized.

The major stimulus for the biosynthesis of testosterone in the Leydig cell is the gonadotrophic hormone, luteinizing hormone (LH). LH is secreted from specific cells located in the anterior pituitary and it interacts with specific receptors on the surface of the Leydig cell and initiates the signal for testosterone production. Cellular events occur rapidly in response to the trophic hormone stimulation of Leydig cells, and result in the synthesis and secretion of testosterone. These rapid or acute effects of hormone stimulation occur within minutes and can be distinguished temporally from the slower chronic effects that occur on the order of many hours and that involve mechanisms to increase gene transcription and translation of the steroid hydroxylase cytochrome P450 enzymes involved in the biosynthesis of these steroids.

The rate-limiting enzymatic step in steroidogenesis is the conversion of cholesterol to pregnenolone by the cholesterol side-chain cleavage complex (CSCC) which is localized to the mitochondrial inner membrane (Stone and Hechter, 1954; Karaboyas and Koritz, 1965; Simpson, et al. 1972). However, the delivery of the substrate cholesterol from cellular stores and the outer mitochondrial membrane to the inner mitochondrial membrane and the CSCC is the true regulated, rate-limiting step in this process (Crivello and Jefcoate, 1980; Jefcoate, et al., 1987). Cycloheximide, an inhibitor of protein synthesis, blocks the hormone-induced steroid production in two steroidogenic tissues of the rat; the adrenal and testis (Ferguson, 1963; Garren, et al., 1965; Davis and Garren, 1968; Jefcoate et al., 1974; Mendelson et al., 1975; Cooke, et al., 1975). This block is at the point of transfer of cholesterol from the outer to the inner mitochondrial membrane and the CSCC (Simpson et al., 1972; Privalle et al. 1983). Therefore, acute regulation of steroidogenesis requires de novo protein synthesis (Jefcoate et al., 1986).

During protein import into the mitochondrial matrix, the inner and outer mitochondrial membranes become closely associated and form protein translocation "contact sites" (Schleyer and Neupert, 1985; Schwaiger et al., 1987; Glick, et al., 1991). Phospholipids are transferred from the outer mitochondrial membrane to the inner mitochondrial membrane at these membrane "contact sites" (Simbeni et al., 1990; Simbeni et al., 1991; Ardail et al., 1991). Therefore, the intramitochondrial cholesterol translocation required for steroidogenesis may also occur at membrane contact sites. An increase in intramitochondrial membrane contacts by a hormone-dependent, cycloheximide-sensitive mechanism may regulate cholesterol transport to the CSCC (Jefcoate, et al., 1986). Thus, in the acute regulation of steroidogenesis, a putative function for the newly synthesized regulatory protein may be to facilitate the formation of mitochondrial contact sites that would result in an increased rate of transfer of cholesterol to the inner membrane and CSCC which ultimately would result in the observed increase in the rate of steroid production. However, the search for these cycloheximide-sensitive regulatory protein(s) has been ongoing for nearly 30 years, but, as yet, the mechanism of cholesterol transfer to the CSCC is not known.

The present inventors have previously identified a family of hormone-induced mitochondrial proteins in MA-10 cells that regulate cholesterol delivery to the inner mitochondrial membrane and the CSCC. These proteins have been described as the mitochondrial 37 kDa, 32 kDa, and 30 kDa molecular weight proteins and they are synthesized in response to either LH and hCG or by stimulation with the cAMP analogue, $Bt_2cAMP$ (Stocco and Kilgore, 1988). The 30 kDa species consists of four separate proteins and proteolytic digestion of all four forms indicates that they are all modified forms of the same protein (Stocco and Chen, 1991). Pulse chase experiments and tryptic peptide mapping of the 37 kDa and 30 kDa proteins indicated that the 37 kDa form is a precursor to the 30 kDa protein (Stocco and Sodeman, 1991; Epstein and Orme-Johnson, 1991). These reports, however, lack information regarding the structure of the nucleic acid molecules and protein molecules involved in steroidogenesis.

Lipoid congenital adrenal hyperplasia (LCAH) is a lethal autosomal recessive disease that results in a complete inability of a newborn infant to synthesize steroids. The lack of mineralocorticoids and glucocorticoids results in death within days to weeks of birth if not detected and treated with adequate steroid hormone replacement therapy. This condition is manifested by the presence of large adrenals containing very high levels of cholesterol and cholesterol esters and also by an increased amount of lipid accumulation in testicular Leydig cells, though this level is somewhat lower than that seen in adrenals. As isolated, mitochondria from adrenals and gonads of affected patients cannot convert cholesterol to pregnenolone (Camacho et al., 1968; Degenhart et al., 1972; Koizumi et al.,; Hauffa et al., 1985). The P450scc enzyme that converts cholesterol to pregnenolone has been shown to be normal in patients who suffered from this disease (Lin et al., 1991). Thus, the defect lies upstream of P450scc at the point of cholesterol delivery to the enzyme.

Prior art lacks sufficient identification of the agent(s) responsible for the LCAH metabolic defect and defects in cholesterol transport, lacks screening methods for their detection, and lacks provision of pharmacological agents effective in alleviating the defects. Because of these problems, known procedures are not completely satisfactory despite efforts of persons skilled in the art, and the present inventors have searched for improvements. Further characterization of agents involved in these defects at the amino acid and nucleic acid levels would provide potential solutions and alternatives to resolving these and other problems in the art.

SUMMARY OF THE INVENTION

The present invention seeks to overcome these and other drawbacks inherent in the prior art by providing compositions and methods including the nucleotide sequence of the gene encoding a steroidogenic acute regulatory protein (StAR) protein, and the amino acid sequence of the StAR protein. The fundamental importance of the StAR protein is that it is the acute regulator of a key step in the steroidogenic biosynthetic pathway. Importantly, the production of mineralocorticoids, glucocorticoids, and sex hormones are dependent on the expression of this protein.

Nucleic acid molecules having nucleotide sequences of the gene encoding StAR may be used in a variety of different diagnostic applications, including the evaluation of gene defects associated with steroid hormone production. The hormonally induced, CAMP-mediated acute regulation of steroid hormone biosynthesis in steroidogenic cells is characterized by the mobilization of cholesterol from cellular stores to the mitochondria outer membrane, and its translocation to the inner membrane where the conversion of cholesterol to pregnenolone occurs. Steroid hormone-dependent disorders that may be addressed using compositions and methods of the present invention include lipoid congenital adrenal hyperplasia, infertility, sexual maturation, androgen-responsive tumors, precocious puberty, McCune-Albright syndrome, adrenal-hypoplasia congenita, or hypogonadotropic hypogonadism.

Further, in pregnancy induced diabetes, progesterone levels are lower than normal and the fetus may be aborted spontaneously. The level of StAR protein may be deficient in these patients and it may be possible as a result of the present invention to monitor levels of StAR in pregnancy for predicting patients that may be at risk for spontaneous abortion.

In certain aspects, the invention relates to a purified nucleic acid molecule having a nucleotide sequence encoding a steroidogenic acute regulatory protein, the protein having an amino acid sequence essentially as set forth in SEQ ID NO: 2. "Purified" nucleic acid molecule having a nucleotide sequence encoding steroidogenic acute regulatory protein (StAR), as used herein, means a StAR encoding nucleic acid molecule substantially free of nucleic acid molecules not encoding an amino acid sequence essentially as set forth in SEQ ID NO:2. A further embodiment of the invention is a purified nucleic acid molecule having a nucleotide sequence encoding a steroidogenic acute regulatory protein antigen, the antigen having an amino acid sequence essentially as set forth in SEQ ID NO:2, and the nucleic acid molecule being substantially free of nucleic acid molecules not encoding the steroidogenic acute regulatory protein antigen.

The term "amino acid sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined as a protein having a sequence essentially as set forth in SEQ ID NO:2, and that is involved in the transfer of cholesterol from cellular stores to the inner mitochondrial membrane. Accordingly, sequences which have between about 70% and about 80%; or more preferably, between about 81% and about 90%; or even more preferably, between about 91% and about 99%; of amino acids that are identical or functionally equivalent to the amino acids of SEQ ID NO:2 will be sequences which are "essentially as set forth in SEQ ID NO:2".

A preferred embodiment is the above-described nucleic acid molecule wherein the steroidogenic acute regulatory protein has the amino acid sequence of SEQ ID NO: 2. An even more preferred embodiment is the above-described nucleic acid molecule wherein the amino acid sequence begins with amino acid methionine at position 48 of SEQ ID NO:2 and extends through amino acid cysteine at position 284 of SEQ ID NO:2. Amino acids 1–47 constitute the signal sequence which is cleaved during processing to the mature protein as described in Example 2.

A further preferred embodiment of the present invention is where the nucleic acid molecule has a nucleotide sequence as set forth in SEQ ID NO:1, and preferably, the nucleic acid molecule is further defined as including a detectable label.

Nucleic Acids

A preferred embodiment of the present invention is a purified nucleic acid molecule that encodes StAR protein having an amino acid sequence in accordance with SEQ ID NO:2. As used herein, the terms "nucleic acid molecule" may refer to a DNA or RNA molecule which has been isolated free of total genomic DNA, or free of total RNA, of a particular species. Therefore, a "purified" nucleic acid molecule as used herein, refers to a nucleic acid molecule that contains a StAR coding sequence yet is isolated away from, or purified free from, total genomic DNA or total RNA, for example, total human genomic DNA. Included within the term "DNA molecule", are DNA segments and smaller fragments of such segments, and also recombinant vectors, including, for example, plasmids, cosmids, phage, viruses, and the like.

Another embodiment of the present invention is a purified nucleic acid molecule, further defined as including a nucleotide sequence in accordance with SEQ ID NO:1. In a more preferred embodiment the purified nucleic acid segment consists essentially of the nucleotide sequence of SEQ ID NO:1. Such nucleotide sequences are more particularly defined as being substantially free of nucleic acids not encoding the StAR protein.

Similarly, a DNA molecule comprising an isolated or purified StAR gene refers to a DNA molecule including StAR coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences or combinations thereof. "Isolated substantially away from other coding sequences" means that the gene of interest, in this case the StAR encoding gene, forms the significant part of the coding region of the DNA molecule, and that the DNA molecule does not contain large portions of naturally-occurring coding DNA, such as large chromosomal fragments or other functional genes or cDNA coding regions. Of course, this refers to the DNA molecule as originally isolated, and does not exclude genes or coding regions later added to the segment by the hand of man.

Another preferred embodiment of the present invention is a purified nucleic acid molecule that encodes a protein in accordance with SEQ ID NO:2, further defined as a recombinant vector. As used herein, the term "recombinant vector", refers to a vector that has been modified to contain a nucleic acid segment that encodes a StAR protein, or fragment of interest thereof. The recombinant vector may be further defined as an expression vector comprising a promoter operatively linked to said StAR encoding nucleic acid molecule. In particular embodiments, the recombinant vector comprises a nucleic acid sequence in accordance with SEQ ID NO:1. By way of example and not limitation, vectors may be further defined as a pCMV, pUC and derivatives thereof, SV40, adenoviral, retroviral, yeast plasmids, Baculovirus or Vaccinia virus vector.

A further preferred embodiment of the present invention is a host cell, made recombinant with a recombinant vector comprising a StAR gene. The recombinant host cell may be a prokaryotic or a eukaryotic cell. In a more preferred embodiment, the recombinant host cell is a eukaryotic cell. As used herein, the term "engineered" or "recombinant" cell is intended to refer to a cell into which a recombinant gene, such as a gene encoding StAR, has been introduced. Therefore, engineered cells are distinguishable from naturally occurring cells which do not contain a recombinantly introduced gene. Thus, engineered cells are cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene, or combinations thereof. Preferred host cells may be further defined as a Leydig cell (primary or MA-10 cells), an adrenalcortical cell such as the H295 human adrenalcortical cell line, a primary culture ovarian granulosa cell, a COS cell, *Saccharomyces cerevisiae*, or *Escherichia coli* cell.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

In certain embodiments, the invention concerns isolated DNA molecules and recombinant vectors which encode a protein or peptide that includes within its amino acid sequence an amino acid sequence essentially as set forth in SEQ ID NO:2. Naturally, where the DNA segment or vector encodes a full length StAR protein, or is intended for use in expressing the StAR protein, the most preferred sequences are those which are essentially as set forth in SEQ ID NO:2.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1", is used in the same sense as described above and means that the nucleic acid sequence substantially corresponds to a portion of SEQ ID NO:1, and has relatively few codons which are not identical, or functionally equivalent, to the codons of SEQ ID NO:1. The term "functionally equivalent codon" is used herein to refer to codons that encode the same amino acid, such as the six codons for arginine or serine, as set forth in Table 1, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes. The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably.

Excepting intronic or flanking regions, and allowing for the degeneracy of the genetic code, sequences which have between about 70% and about 80%; or more preferably, between about 80% and about 90%; or even more preferably, between about 90% and about 99%; of nucleotides which are identical to the nucleotides of SEQ ID NO:1 will be sequences which are "essentially as set forth in SEQ ID NO:1". Sequences which are essentially the same as those set forth in SEQ ID NO:1 may also be functionally defined as sequences which are capable of hybridizing to a nucleic acid segment containing the complement of SEQ ID NO:1 under relatively stringent conditions. Suitable relatively stringent hybridization conditions will be well known to those of skill in the art and are clearly set forth herein, for example conditions for use with Northern blot analysis, and as described in the preferred embodiments and in Example 2.

TABLE 1

CODON DEGENERACY

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |

TABLE 1-continued

CODON DEGENERACY

| Amino Acids | | | Codons | | | | | |
|---|---|---|---|---|---|---|---|---|
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The present invention includes a purified nucleic acid molecule complementary, or essentially complementary, to the nucleic acid molecule having the sequence set forth in SEQ ID NO:1. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1 under relatively stringent conditions such as those described herein in the detailed description of the preferred embodiments. Complementary nucleotide sequences are useful for detection and purification of hybridizing nucleic acid molecules. A preferred embodiment of the invention is a molecule complementary to SEQ ID NO: 1 and is a cDNA molecule complementary to a steroidogenic acute regulatory protein mRNA.

The present inventors also envision the preparation of fusion proteins and peptides, e.g., where the StAR coding regions are aligned within the same expression unit with other proteins or peptides having desired functions, such as for purification or immunodetection purposes (e.g., proteins which may be purified by affinity chromatography and enzyme label coding regions, respectively).

StAR protein has been successfully expressed in eukaryotic expression systems by the present inventors, especially using the PCMV vector in COS cells. Other expression systems contemplated by the present inventors include, e.g., baculovirus-based, glutamine synthase-based, dihydrofolate reductase-based systems, or the like. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the StAR gene, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of StAR in accordance herewith. Examples include cell lines typically employed for eukaryotic expression such as COS, CHO, MA-10 cells, or *Saccharomyces cerevisiae*.

It is proposed that transformation of host cells with DNA segments encoding the StAR protein will provide a convenient means for obtaining purified StAR protein. It is also proposed that cDNA, genomic sequences, and combinations thereof, are suitable for eukaryotic expression, as the host cell will process the genomic transcripts to yield functional mRNA for translation into protein. A preferred embodiment of the invention is a composition comprising a purified RNA molecule having a nucleotide sequence of SEQ ID NO:14.

Nucleic Acid Hybridization and PCR reactions.

Oligonucleotide sequences based on the mouse or a homologous sequence of StAR may be used as primers in a polymerase chain reaction to screen for possible mutations in StAR mRNA causing a variety of pathologies, for example, the lethal human disease, lipoid congenital adrenal hyperplasia. Therefore, StAR nucleic acid sequence can be applied to screen prenatal, perinatal, or neonatal DNA for possible mutations in StAR. If the disease is detected early, then continual mineralocorticoid, glucocorticoid, or steroid replacement therapy can prolong the life of the patient. Further applications will arise when additional disease states are linked to mutations in the StAR gene, or under conditions where mutations in related genes result in decreased levels of StAR mRNA or protein. In these cases, analysis of StAR mRNA or protein has significant diagnostic value.

DNA probes and primers useful in hybridization studies and PCR reactions may be derived from any portion of SEQ ID NO:1 and are generally at least about seventeen nucleotides in length. Therefore, probes and primers are specifically contemplated that comprise nucleotides 1 to 17, or 2 to 18, or 3 to 19 and so forth up to a probe comprising the last 17 nucleotides of the nucleotide sequence of SEQ ID NO:1. Thus, each probe would comprise at least about 17 linear nucleotides of the nucleotide sequence of SEQ ID NO:1, designated by the formula "n to n+16," where n is an integer from 1 to about 1435. Longer probes that hybridize to the StAR gene under low, medium, medium-high and high stringency conditions are also contemplated, including those that comprise the entire nucleotide sequence of SEQ ID NO:1. Selected oligonucleotide subportions of the gene encoding StAR have significant utility irrespective of whether they encode antigenic peptides. In these aspects, it is contemplated, for example, that shorter or longer nucleic acid fragments of the StAR gene, prepared synthetically, recombinantly, or otherwise, can be employed as hybridization probes. Such probes can be readily employed in a variety of ways, including their use in the identification of genes encoding StAR in biological tissues or clinical samples, as well as in the detection and evaluation of StAR in pathologies that relate to cholesterol and/or steroid synthesis. Biological or clinical samples include, but are not limited to, biopsy specimens from adrenal or gonadal tissue, or blood, for example.

A general method for preparing oligonucleotides of various lengths and sequences is described by Caracciolo et al. (1989). In general, there are two commonly used solid phase-based approaches to the synthesis of oligonucleotides containing conventional 5'-3' linkages, one involving intermediate phosphoramidites and the other involving intermediate phosphonate linkages. In the phosphoramidite synthesis a suitably protected nucleotide having a cyanoethylphosphoramidate at the position to be coupled is reacted with the free hydroxyl of a growing nucleotide chain derivatized to a solid-support. The reaction yields a cyanoethylphosphite, which linkage must be oxidized to the cyanoethylphosphate at each intermediate step, since the reduced form is unstable to acid.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete.

The phosphonates can also be converted to phosphoramidate derivatives by reaction with a primary or secondary amine in the presence of carbon tetrachloride. To indicate the two approaches generically, the incoming nucleotide is regarded as having an "activated" phosphite/phosphate group. In addition to employing commonly used solid phase synthesis techniques, oligonucleotides may also be synthesized using solution phase methods such as triester synthesis. The methods are workable, but in general, less efficient for oligonucleotides of any substantial length.

Preferred oligonucleotides resistant to in vivo hydrolysis may contain a phosphorothioate substitution at each base. Oligodeoxynucleotides or their phosphorothioate analogues may be synthesized using an Applied Biosystem 380B DNA synthesizer (Applied Biosystems, Inc., Foster City, Calif.).

A further embodiment of the invention is a purified nucleic acid molecule having at least a 17, 20, 25, 30, 50, 100, 200, 500, or 1000 nucleotide sequence that corresponds to, or is capable of hybridizing to the nucleic acid sequence of SEQ ID NO:1 under conditions standard for hybridization fidelity and stability. Furthermore, it is contemplated that nucleic acid molecules having a nucleotide sequence of SEQ ID NOS:1, 9, 10, 11, 12, or 13 for stretches of between about 10 nucleotides to about 20 or to about 30 nucleotides will find particular utility, with even longer sequences, e.g., 40, 50, 150, 250, 450, even up to full length, being more preferred for certain embodiments. The ability of such nucleic acid probes to specifically hybridize to StAR nucleic acid sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

These probes will be useful in hybridization embodiments, such as Southern and Northern blotting. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 20 and about 40 nucleotides, or even up to the full length of the nucleic acid as shown in SEQ ID NOS: 1 and 9–13 according to the complementary sequences one wishes to detect.

The use of a hybridization probe of about 10 nucleotides in length allows the formation of a duplex molecule that is both stable and selective. Molecules having complementary sequences over stretches greater than 10 bases in length are preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,683,202 (herein incorporated by reference) or by introducing selected sequences into recombinant vectors for recombinant production.

Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt andor high temperature conditions, such as provided by 0.02M–0.15M NaCl at temperatures of 50° C. to 70° C. Such selective conditions tolerate little, if any, mismatch between the probe and the template or target strand.

Where one desires to prepare mutants employing a mutant primer strand hybridized to an underlying template or where one seeks to isolate sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptides from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length in the order of about 2000 nucleotides for a protein or otherwise biologically active equivalent peptide having at least a sufficient portion of the sequence in accordance with SEQ ID NO:2 capable of providing said StAR-biological activity.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid and amino acid sequences having sequence identifiers as listed in Table 2. Therefore, DNA segments prepared in accordance with the present invention may also encode biologically functional equivalent proteins or peptides which have variant amino acid sequences. Such sequences may arise as a consequence of codon redundancy and functional equivalency which are known to occur naturally within nucleic acid sequences and the proteins thus encoded. Alternatively, functionally equivalent proteins or peptides may be constructed via the application of recombinant DNA technology, in which changes in the protein structure may be engineered, based on considerations of the properties of the amino acids being exchanged.

Any of a variety of steroidogenic cells may be used as a source to prepare the purified StAR protein of the invention having an amino acid sequence essentially as set forth in SEQ ID NO:2. By way of example, particularly useful cells include adrenal fasciculata, adrenal glomerulosa, corpus luteum cells, ovarian theca, ovarian granulosa, mouse Y-1 adrenalcortical tumor cells, primary Leydig cell cultures and MA-10 Leydig tumor cells. Most preferably, the cell line employed to prepare a mitochondrial extract for purposes of isolating the herein described StAR protein is primary Leydig cell cultures and MA-10 Leydig tumor cells.

Table 2 lists the identity of sequences of the present disclosure having sequence identifiers.

TABLE 2

Identification of Sequences Having Sequence Identifiers

| SEQ ID NO: | IDENTITY |
| --- | --- |
| 1 | DNA sequence encoding StAR |
| 2 | Protein sequence of 30kDa StAR |
| 3 | peptide 23 |
| 4 | peptide 25 |
| 5 | peptide 45 |
| 6 | Asn Gln Glu Gly Trp Lys |
| 7 | Ala Glu His Gly Pro Thr Cys Met Val |
| 8 | amino acids 88–98 of SEQ ID NO:2 |
| 9 | degenerate oligonucleotides made to peptide 23; coding direction |
| 10 | degenerate oligonucleotides made to peptide 23; noncoding direction |
| 11 | degenerate oligonucleotides made to peptide 25; coding direction |

TABLE 2-continued

Identification of Sequences Having Sequence Identifiers

| SEQ ID NO: | IDENTITY |
| --- | --- |
| 12 | degenerate oligonucleotides made to peptide 25; noncoding direction |
| 13 | PCR product, nucleotides 343–743 of SEQ ID NO:1 |
| 14 | RNA sequence encoding StAR |

StAR Protein Compositions

In particular aspects, the present invention provides a purified StAR protein having an amino acid sequence essentially as set forth in SEQ ID NO:2. In a further embodiment of the composition, the amino acid sequence begins at the amino acid methionine at position 48 of SEQ ID NO:2 and extends through amino acid cysteine at position 284 of SEQ ID NO:2.

The StAR protein may be phosphorylated or unphosphorylated. The mature 30 kDa form of StAR protein has four different isoelectric species, designated as 30 kDa 1, 2, 3, and 4, with 1 being the most basic form and 4 the most acidic form. Studies by the present inventors demonstrated that forms 3 and 4 were phosphorylated forms of 1 and 2, and that phosphorylation is important for biological activity. These forms of the 30 kDa protein are useful as molecular weight standards, and as standards for isoelectric focusing. Threonine, serine, and tyrosine amino acids are most frequently those amino acids in a protein that are phosphorylated, and in the case of the StAR protein, a threonine may be phosphorylated.

The purified 37 kDa StAR protein is expected to have many different uses, including, for example, supplementing a patient lacking StAR activity to provide proper cholesterol transport and subsequent synthesis of steroids.

In some aspects of the peptides of the StAR protein, the peptides comprise an amino acid sequence in accordance with SEQ ID NO:3, 4, 5, 6, 7, or 8. These peptides are useful for designing oligonucleotides for screening and for identifying antigenic determinants of the StAR protein (see examples). Peptides having less than about 45 amino acid residues may be chemically synthesized by the solid phase method of Merrifield (1963), which reference is specifically incorporated by reference herein, using an automatic peptide synthesizer with standard t-butoxycarbonyl (t-Boc) chemistry that is well known to one skilled in this art in light of this disclosure. The amino acid composition of the synthesized peptides may be determined by amino acid analysis with an automated amino acid analyzer to confirm that they correspond to the expected compositions. The purity of the peptides may be determined by sequence analysis or HPLC.

In still another embodiment of the present invention, methods of preparing a StAR protein composition are provided. In one aspect, the method comprises growing recombinant host cells comprising a vector that encodes a protein which includes an amino acid sequence in accordance with SEQ ID NO:2, under conditions permitting nucleic acid expression and protein production followed by recovering the protein so produced. The host cell, conditions permitting nucleic acid expression, protein production and recovery, will be known to those of skill in the art, in light of the present disclosure of the StAR gene. A preferred host cell is a COS cell.

Modifications and changes may be made in the sequence of the StAR peptides or protein of the present invention and still obtain a peptide or protein having like or otherwise desirable characteristics. For example, certain amino acids may be substituted for other amino acids in a peptide without appreciable loss of function. Since it is the interactive capacity and nature of an amino acid sequence that defines the peptide's functional activity, certain amino acid sequences may be chosen (or, of course, its underlying DNA coding sequence) and nevertheless obtain a peptide with like properties. It is thus contemplated by the inventors that certain changes may be made in the sequence of a StAR peptide or protein (or underlying DNA) without appreciable loss of its ability to function.

Substitution of like amino acids can be made on the basis of hydrophilicity. U.S. Pat. No. 4,554,101, incorporated herein by reference, states that the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent peptide. In such changes, the substitution of amino acids whose hydrophilicity values are within ±2 is preferred, those which are within ±1 are more preferred, and those within ±0.5 are most preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate= Glu (E); Glutamine=Gln (Q); Glycine=Gly (G); Histidine= His (H); Isoleucine=Ile (I); Leucine=Leu (L); Lysine=Lys (K); Methionine=Met (M); Phenylalanine=Phe (F); Proline= Pro (P); Serine=Ser (S); Threonine=Thr (T); Tryptophan= Trp (W); Tyrosine=Tyr (Y); Valine=Val (V).

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

Another aspect of the invention is a method of preparing a steroidogenic acute regulatory protein encoded by the purified nucleic acid molecule having a nucleotide sequence of SEQ ID NO:1, the method comprising the steps of preparing a recombinant host bearing the nucleic acid molecule, the host being capable of expressing the protein, culturing the recombinant host to produce steroidogenic acute regulatory protein, and collecting the steroidogenic acute regulatory protein having an amino acid sequence essentially as set forth in SEQ ID NO:2. In one aspect, the recombinant host is a COS cell.

A further embodiment of the present invention relates to a purified nucleic acid molecule encoding StAR protein having an amino acid sequence essentially as set forth in SEQ ID NO: 2, said nucleic acid molecule obtained by a process of; i) preparing oligonucleotides that encode a segment of an amino acid sequence of SEQ ID NO:2 and that have at least about 17 nucleotides; ii) screening an animal cell DNA library with said oligonucleotides; and iii) obtaining the purified nucleic acid molecule encoding StAR protein having an amino acid sequence essentially as set forth in SEQ ID NO: 2.

Pharmaceutical Preparations.

Another aspect of the present invention provides therapeutic agents for the treatment of steroid hormone-dependent disorders in an animal. The therapeutic agent comprises an admixture of StAR peptide or protein in a pharmaceutically acceptable excipient. Most preferably, the therapeutic agent will be formulated so as to be suitable for injection. Pharmacologically active peptides of StAR may also be provided to a subject via gene therapy. Many different vehicles exist for accomplishing this end, such as incorporation of the StAR gene, or fragment thereof, into an adenovirus, retrovirus, or other techniques known to those of skill in the art in light of the present disclosure. Ex vivo gene therapy is also contemplated as another mode of administration.

Such preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The active compounds may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. See, for example, Remington (1995), which reference is incorporated by reference herein.

Antibodies.

In another aspect, the present invention includes an antibody that is immunoreactive with a StAR polypeptide as described for the invention. An antibody can be a polyclonal or a monoclonal antibody. In some embodiments, the antibody is a monoclonal antibody. Means for preparing and characterizing antibodies are well known in the art (See, e.g., Antibodies "A Laboratory Manual, E. Howell and D. Lane, Cold Spring Harbor Laboratory, 1988). A preferred polyclonal antibody has binding specificity for amino acids 1–26, 10–26, 36–47, or 88–98 of SEQ ID NO:2.

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for the peptides of the present invention may be prepared using conventional immunization techniques, as will be generally known to those of skill in the art. A composition containing antigenic epitopes of the peptide sequences, isolated peptides, or fragments thereof can be used to immunize one or more experimental animals, such as a rabbit or mouse, which will then proceed to produce specific antibodies against StAR. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with a purified peptide composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against the desired peptide. Hybridomas which produce monoclonal antibodies to the selected antigens are identified using standard techniques, such as ELISA and Western blot methods.

Hybridoma clones can then be cultured in liquid media and the culture supernatants purified to provide the peptide-specific monoclonal antibodies. In general, monoclonal antibodies to the peptide antigen can be used in the identification of steroid hormone-dependent disorders. It is proposed that the monoclonal antibodies of the present invention will find useful application in standard immunochemical procedures, such as ELISA and Western blot methods, as well as other procedures which may utilize antibody specific to common or allelically distinct peptide epitopes.

Monoclonal and polyclonal antibodies raised against peptides or protein of the present examples are useful for (1) screening a cDNA expression library in the process of cloning a gene that encodes a particular protein or related protein (for example, the SUPERSCREEN® immuno-screening system from AMERSHAM®), (2) facilitating the purification of a particular protein or related protein by using column chromatography to which the monoclonal antibody is bound, and (3) providing reagents necessary for a diagnostic immunoassay for screening biological samples.

Monoclonal antibodies are obtained using the following procedure:

Immunization Schedule for Raising Monoclonal Antibodies
1. For each mouse, mix 250 µl of antigen solution containing 10 µg of antigen with 250 µl of complete Freund's adjuvant. Inject six BALB/c female mice ip (intraperitoneal injection).
2. After 14 days, repeat the injections of antigen and incomplete Freund's adjuvant.
3. Collect tail bleeds from immunized mice on day 24. Do 1 in 5 dilutions in phosphate buffered saline (PBS) and test all samples by comparison with similar dilutions of normal mouse serum in a dot blot.
4. On day 35, inject all animals ip with antigen and incomplete Freund's.
5. Day 45, do tail bleeds and test by dot blot. All serum samples checked by immunoprecipitation against in vivo radiolabeled antigen preparation.
6. Day 56, inject best responder, 100 µl iv and 100 µl ip. All others get ip injection with incomplete Freund's.
7. Day 59, fuse splenocytes from best responder.

In still another embodiment of the invention, a hybridoma cell line which produces a monoclonal antibody which specifically binds StAR protein is provided. Most particularly, the hybridoma cell line is an animal hybridoma cell line prepared by a process of immunizing an animal, such as a mouse or a rat, with StAR protein, isolating anti-StAR antibody producing cells from the immunized animal, and fusing the antibody producing cells with a neo-plastic animal cell line to obtain a hybridoma cell line. The resultant hybridoma tissue culture supernatants are screened for monoclonal antibodies as follows:

1. A protein solution of at least 1 µg/ml of antigen is added to a nitrocellulose sheet at 0.1 ml/cm². Allow the protein to bind to the paper for 1 hr. Higher concentrations of proteins will increase the signal and make screening faster and easier. If the amount of protein is not limiting, concentrations of 10–50 µg/ml should be used. Nitrocellulose can bind approximately 100 µg of protein per cm².
2. Wash the nitrocellulose sheet three times in PBS.
3. Place the sheet in a solution of 3% BSA in PBS with 0.02% sodium azide for 2 hr to overnight. To store the sheet, wash twice in PBS and place at 4° C. with 0.02% sodium azide.

For long-term storage, shake off excessive moisture from the sheet, cover in plastic wrap, and store at −70° C.

4. Place the wet sheet on a piece of parafilm, and rule with a soft lead pencil in 3-mm squares. Cut off enough paper for the number of assays.

5. Apply 1 μl of the hybridoma tissue culture supernatant to each square. Incubate the nitrocellulose sheet on the parafilm at room temperature in a humid atmosphere for 30 min.

Along with dilutions of normal mouse serum, include dilutions of the mouse serum from the last test bleed as controls. Dilutions of the test sera are essential to control correctly for the strength of the positive signals. Mouse sera will often contain numerous antibodies to different regions of the antigen and therefore will give a stronger signal than a monoclonal antibody. Therefore, dilutions need to be used to lower the signal. Good monoclonal antibodies will appear 10-fold less potent than good polyclonal sera.

6. Quickly wash the sheet three times with PBS, then wash two times for 5 min each with PBS.
7. Add 50,000 cpm of $^{125}$I-labeled rabbit anti-mouse immunoglobulin per 3-mm square in 3% BSA/PBS with 0.02% sodium azide (about 2.0 ml/cm$^2$).
8. After 30–60 min of incubation with shaking at room temperature, wash extensively with PBS until counts in the wash buffer approach background levels.
9. Cover in plastic wrap and expose to X-ray film with a screen at −70° C.

The hybridoma identified as producing antibody to the protein of interest is passaged as follows:

1. Inject 10$^7$ (or less) cells into female mice that have been injected ip about 1 week earlier with 0.5 ml of pristane or incomplete Freund's adjuvant. These types of injections are also used to prime mice for ascites production, and this may serve as a convenient source of appropriate hosts. If no mice are available, inject mice with incomplete Freund's adjuvant and wait 4 hr to 1 day before injecting the hybridoma cells. The animals must be of the same genetic background as the cell line.
2. If an ascites develops, tap the fluid and transfer into a sterile centrifuge tube.
3. Spin the ascites at 400 g for 5 min at room temperature.
4. Remove the supernatant. Resuspend the cell pellet in 10 ml of medium supplemented with 10% fetal bovine serum and transfer to a tissue culture plate. The supernatant can be checked for the presence of the antibody and used for further work if needed.
5. Handle as for normal hybridomas, except keep the cells separate from the other cultures until there is little chance of the contamination reappearing.

The present invention in still another aspect defines an immunoassay for the detection of a StAR protein in a biological sample. In one particular embodiment of the immunoassay, the immunoassay comprises; preparing an antibody having binding specificity for StAR protein to provide an anti-StAR antibody, incubating the anti-StAR antibody with the biological sample for a sufficient time to permit binding between antibody and StAR present in said biological sample, and determining the presence of bound antibody by contacting the incubate of the sample and antibody with a detectably labeled antibody specific for the anti-StAR antibody, wherein the presence of anti-StAR antibody in the biological sample is detectable as the measure of the detectably labeled antibody from the biological sample. In some embodiments, the antibody is preferably a monoclonal antibody having binding specificity for the StAR amino acid sequence 88–98 of SEQ ID NO:2.

By way of example, the antibody may be labeled with any of a variety of detectable molecular labeling tags. Such include, an enzyme-linked antibody, a fluorescent-tagged antibody, or a radio-labelled antibody.

A further embodiment of the invention is a method for detecting a chromosomal genetic lesion comprising the steps of i) preparing a nucleic acid probe having a nucleotide sequence that includes at least a 17-base segment of SEQ ID NO:1; ii) contacting a chromosomal sample with the probe to allow hybridization of the sample to the probe under conditions standard for hybridization fidelity and stability, wherein lack of specific hybridization of the probe and the chromosomal sample provides for detection of a potential genetic lesion in the chromosome. The genetic lesion may be a deletion, a rearrangement, an insertion, a transition, a transversion, a frameshift, a missense or a nonsense mutation. In particular, the genetic lesion correlates with the presence of lipoid congenital adrenal hyperplasia. Human tissue samples may be biopsy material from adrenal tissue, gonadal tissue, or blood.

In another aspect of the invention, a screening method for lipoid congenital adrenal hyperplasia is provided. The method comprises the steps of i) obtaining a chromosomal sample to provide a test sample; ii) preparing a nucleic acid probe having a nucleotide sequence essentially as set forth in SEQ ID NO:1; and, iii) contacting the test sample with the nucleic acid probe under hybridization conditions allowing for detection of a mismatch in a hybridizing molecule as a screening method for lipoid congenital adrenal hyperplasia. A mismatch is determined most readily by determining the nucleotide sequence of the hybridizing molecule, a difference in the nucleotide sequence of the hybridizing molecule and the nucleotide sequence of SEQ ID NO:1 provides a screen for lipoid congenital adrenal hyperplasia.

Further embodiments of the invention include; a method for stimulating cholesterol transport, a method for increasing production of progesterone, and a method for increasing steroidogenesis; these methods comprise administering a pharmacologically effective amount of steroidogenic acute regulatory protein having an amino acid sequence essentially as set forth in SEQ ID NO:2. Progesterone is used clinically in a variety of applications in males and females. Methods for providing enhanced production of progesterone are thus a valuable application of the StAR compositions of the present invention. The protein may be delivered by recombinant means, i.e., synthesis from an expression vector containing nucleic acid sequences encoding the protein.

Following long-standing patent law convention, the terms "a" and "an" mean "one or more" when used in this application, including the claims.

Abbreviations

Bt$_2$cAMP: N$^6$, 2'-O-dibutyryladenosine-3':5'-cyclic monophosphate
CHAPS: 3-[3-cholamidopropyl dimethylammonio] 1-propanesulfonate
CSCC: cholesterol side-chain cleavage
DBI: diazepam binding inhibitor
hCG: human chorionic gonadotropin
HPLC: high performance liquid chromatography
IOD integrated optical density
LH: luteinizing hormone
Mops: 3-[N-Morpholino]propane-sulfonic acid
PAGE: polyacrylamide gel electrophoresis
PBR peripheral benzodiazepine receptor
PBS: Dulbecco's phosphate-buffered saline with calcium and magnesium
PCR: polymerase chain reaction
SAP: steroidogenesis activator polypeptide
SCP$_2$: sterol carrier protein 2
WAY: Waymouth's MB 752 media

DETAILED DESCRIPTION OF THE PREFERRED EMBODIMENTS

The present inventors have utilized the MA-10 mouse Leydig tumor cell line to study the acute regulation of steroidogenesis. Specifically, the inventors have identified a family of hormone-induced mitochondrial proteins in MA-10 cells that regulate cholesterol delivery to the inner mitochondrial membrane and the CSCC. These proteins have been described as the mitochondrial 37 kDa, 32 kDa, and 30 kDa molecular weight proteins and they are synthesized in response to either LH and HCG or by stimulation with the CAMP analogue, $Bt_2cAMP$. The 30 kDa species consists of four separate proteins and proteolytic digestion of all four forms indicates that they are all modified forms of the same protein. Pulse chase experiments and tryptic peptide mapping of the 37 kDa and 30 kDa proteins indicated that the 37 kDa form is a precursor to the 30 kDa protein.

The following data support the involvement of these proteins in the acute regulation of steroidogenesis: i) their synthesis is directly correlated to the capacity of the MA-10 cells to produce steroid in response to hormone stimulation in both a time and dose responsive manner; ii) their synthesis is sensitive to cycloheximide; iii) the 30 kDa proteins are localized to the mitochondria and are processed from a larger precursor protein of 37 kDa; iv) a rat Leydig tumor cell line ($R_2C$) which constitutively produces steroids constitutively expresses the 30 kDa proteins; and v) inhibition of steroidogenesis is concomitant with inhibition of synthesis of 30 kDa proteins (Stocco and Kilgore, 1988; Stocco and Chaudhary, 1990; Stocco and Chen, 1991; Stocco and Sodeman, 1991;Stocco, 1992; Stocco and Ascoli, 1993; Stocco et al., 1993; Stocco and Clark, 1993).

The present inventors have now cloned the cDNA for this family of proteins, and have also more directly determined their function in the regulation of steroid production, particularly in MA-10 cells.

The following examples describe the purification of the MA-10 30 kDa proteins and the isolation and characterization of a full length cDNA clone. The cDNA encodes a novel mouse protein of 31.6 kDa, which relates to the previously described 37 kDa precursor protein of the LH-induced family of mitochondrial proteins. The amino acid sequence at the amino terminus has been identified by the present inventors to be characteristic of a mitochondrial targeting signal. Using an in vitro transcription/translation system, the precursor protein was processed and modified to all forms of the 30 kDa proteins by isolated mitochondria. Immunoblot analysis of mitochondria isolated from either $Bt_2cAMP$-stimulated MA-10 cells or MA-10 cells transfected with the cDNA confirmed the cDNA encodes the same immunospecific 30 kDa protein. In addition, in the absence of hormone stimulation, expression of the 30 kDa protein in MA-10 cells resulted in a 1.5–3.5 increase in progesterone production above cells transfected with vector alone. Thus, the present inventors have demonstrated for the first time that expression of the LH-inducible 30 kDa protein directly results in an increase in steroid biosynthesis. This protein is required in the acute regulation of hormone-induced steroidogenesis.

Materials & Methods. The materials and methods used in the following examples are provided here. In light of these teachings, one of skill in the art would realize that other equivalent materials and methods may be used in the present invention.

Chemicals. Waymouth's MB 752 medium, Dulbecco's modified Eagle's medium, horse serum, fetal bovine serum, antibiotics, and PBS were purchased from Life Technologies, Inc. (Gaithersburg, Md.). $Bt_2cAMP$, leupeptin, aprotinin, phenylmethylsufonyl fluoride, formaldehyde, and *Escherichia coil* alkaline phosphatase were obtained from Sigma (St. Louis, Mo.). Silver nitrate was from Fisher (Houston, Tex.). The ampholines and stock solutions of nucleic acids were purchased from Pharmacia Biotech Inc. (Piscataway, N.J.). Restriction endonucleases, T7 RNA polymerase, RNAsin, and Taq DNA polymerase were purchased from Promega (Madison, Wis.). Radiolabeled nucleotides [$^{32}$-P] CTP and [($^{35}$S]-•methionine were obtained from Du Pont NEN (Boston, Mass.). oligonucleotides were synthesized and purified by Midland Certified Reagent Co. (Midland, Tex.).

Maintenance of MA-10 and COS 1 cells . The MA-10 mouse Leydig tumor cell line was from Dr. M. Ascoli (Dept. of Pharmacology, Univ. of Iowa College of Medicine, Iowa City, Iowa). These cells were derived from the M5480P tumor, they have functional LH/CG receptors and produce large amounts of progesterone rather than testosterone in response to hormone stimulation. The cells were grown in Waymouth's MB/752 media containing 15% horse serum ($WAY^+$) at 37° C. in a humid atmosphere under 5% $CO_2$ and maintained in culture using standard techniques (Ascoli, 1981). COS 1 cells were obtained from the American Type Culture Collection (#CRL 1650) and grown in Dulbecco's modified Eagle's medium high glucose media containing 10% fetal bovine serum and 100 units of penicillin/ml and 10 units of streptomycin sulfate/ml.

Isolation of Mitochondria. MA-10 cells were stimulated for 6 h with 1 mM $Bt_2cAMP$ in Waymouth's media containing 5% horse serum, then washed once with PBS (Life Technologies, Inc.) and collected in 0.25M sucrose, 10 mM Tris, pH 7.4, 0.1 mM EDTA by scraping with a rubber policeman. The cells were lysed by homogenization at 1000 rpm for 25 passes with a Potter Elvehjem homogenizer fitted with a serrated Teflon pestle. The homogenate was centrifuged at 600×g for 30 min, and the resultant supernatant was centrifuged at 9000×g for 30 min to pellet the mitochondria. The mitochondrial pellets were stored frozen at −80° C. until used to purify the 30-kDa proteins.

For the in vitro translation reactions, mitochondria were isolated as above with the following exceptions; MA-10 cells were not stimulated with hormone, and the cells were lysed using a glass-on-glass Dounce homogenizer with fitted pestle and homogenized by hand for 25 passes. The mitochondrial pellet was washed once with import buffer (3% bovine serum albumin, 70 mM KCl, 220 mM sucrose, 10 mM Mops/KOH (pH 7.2), 2.5 mM $MgCl_2$ (Hartl, 1986) then resuspended in 200 μl of the import buffer to a protein concentration of 7.5 mg/ml. Mitochondria were used immediately after isolation for the in vitro translation reaction. Isolation of mitochondria from COS 1 cells for immunoblot analysis was as described (Clark and Waterman, 1991).

Purification of the 30-kDa Proteins from Isolated Mitochondria. In general, mitoplasts (mitochondria stripped of outer membrane) were purified from isolated mitochondria and solubilized with CHAPS detergent. Preparative one-dimensional SDS-PAGE gels were used to isolate CHAPS soluble proteins of 28–32 kDa in size (30-kDa fraction), and the 30-kDa proteins were isolated and recovered by two-dimensional SDS-PAGE of the 30-kDa fraction. A more detailed description of this purification is as follows.

Preparation of Mitoplasts and CHAPS Solubilization. Mitoplasts were prepared using the methods detailed by Ardail et al. (1991). Mitochondria were resuspended in swelling buffer (10 mM potassium phosphate, pH 7.4, 0.1 mM EDTA, 1 mM phenylmethylsulfonyl fluoride, 0.1 mg leupeptin/ml, and 0.04 units aprotinin/ml) to a protein concentration of 2.5 mg/ml, incubated on ice for 20 min, then homogenized 5 times by hand using a glass Dounce homogenizer fitted with a Teflon pestle. An equal volume of swelling buffer containing 30% sucrose was added to the shocked mitochondria and mixed thoroughly. Mitoplasts were recovered by centrifugation at 12,000×g for 30 min, resuspended in swelling buffer to a protein concentration of 2.5 mg/ml, and solubilized by adding a fresh solution of swelling buffer containing 25% CHAPS to achieve a 1:1 mg protein to mg detergent ratio (0.25% CHAPS final concentration). The CHAPS soluble sample was recovered after a 100,000×g centrifugation for 45 min and concentrated under nitrogen pressure using a Filtron stir-cell with 10,000 molecular weight cut off (Pharmacia Biotech Inc.). Protein was determined for each fraction by the method of Bradford (1976).

Preparative One-dimensional SDS-Polyacrylamide Gel Electrophoresis. The CHAPS soluble sample was separated on a preparative 1.5 mm 12.5% SDS-polyacrylamide gel (Laemmli, 1970). A 5 mm section of the polyacrylamide gel corresponding to 28–32 kDa band was excised, and the proteins were electroeluted from the gel and concentrated using the Centrilutor microelectroeluter system (Amicon). The position of the 5 mm strip was determined by running a reference lane containing molecular weight markers and cutting the lane from the gel and staining the markers with Coomassie blue.

Two-Dimensional Polyacrylamide Gel Electrophoresis. Approximately 150–250 µg of the 30-kDa fraction (the concentrated 28–32 kDa proteins from the one-dimensional gel) was resolved by two-dimensional PAGE (O'Farrell, 1975), and the proteins were electrophoretically transferred to nitrocellulose in 20 mM Tris/Cl pH 7.4, 150 mM glycine, 10% β-mercaptoethanol, 0.01% SDS for 4 h at 350 mA (Deutscher, 1990; Towbin, et al. 1979). The nitrocellulose was transiently stained with Ponseau S (0.2% in 1% acetic acid) to visualize and isolate the specific 30 kDa proteins for subsequent amino acid microsequence analysis. The filters were destained with 1% acetic acid, and washed thoroughly with HPLC grade water. The nitrocellulose spots were stored damp at −80° C. until shipped to the Harvard Microchemical facility where the in situ digestion, peptide separation, and microsequence analysis was performed on a fee-for service basis.

Quantitation of Silver Stained Proteins. The two-dimensional SDS-PAGE gels were fixed in 50% methanol, 12% acetic acid for 1 h, then washed with 50% EtOH 3 times for 20 min with each wash. To silver stain the proteins, the gel was pretreated with 0.02% sodium thiosulfate for 1 min, rinsed 3 times with $H_2O$ for 20 s each rinse, then treated with 0.2% silver nitrate, 0.02% formaldehyde for 20 min. After the silver nitrate impregnation, the gel was rinsed with $H_2O$ twice and developed with 6% sodium carbonate, 0.02% formaldehyde. The silver-stained image was captured, and the integrated optical densities (IOD) of the proteins were quantitated using the BioImage Visage 2000 computer-assisted image analysis system (BioImage, Ann Arbor, Mich.). The percent of the total IOD of each spot (protein) was determined automatically and used to quantitate the 30-kDa protein. For example, the percent of total IOD for 30-kDa protein 1×mg total protein loaded onto the first dimension gel/mg total protein for the fraction=mg 30-kDa protein 1 in that fraction.

Preparation of the $Bt_2$cAMP-stimulated MA-10 Mouse Leydig Tumor Cell CDNA library. Total RNA was isolated from 6-h $Bt_2$cAMP-stimulated MA-10 cells by a one-step extraction adapted from the methods of Chomczynski and Sacchi (1987) using RNA STAT-60 (Tel-Test B, Inc., Friendswood, Tex.). Poly $A^+$ mRNA was twice selected on a gravity flow oligo-dT column (5 Prime-3 Prime, Inc.). A λgt22A cDNA library was constructed from the poly$A^+$ RNA using the SuperScript Lambda System for cDNA synthesis and λ cloning (Life Technologies, Inc.). Briefly, first strand synthesis was generated using a NotI Primer-Adapter and SuperScript RT, an engineered Moloney murine leukemia virus reverse transcriptase. Second strand synthesis was generated by nick translation replacement of the template mRNA and a SalI adapter was ligated to the cDNA ends. The cDNAs were digested with NotI and SalI restriction enzymes and cloned into λgt22A. The DNA was packaged in vitro using the λ Packaging System (Life Technologies, Inc.) and the recombinant phages were stored in 50 mM Tris/Cl pH 7.5, 100 mM NaCl, 1 mM $MgSO_4$, 0.01% gelatin and $CHCl_3$ at 4° C. The cDNA library contained $9×10^5$ independent clones. The E. coli strain Y1090r⁻ (Life Technologies, Inc.) was infected with the stock phage solution, and the library was amplified to a titer of $2×10^{10}$ plaque-forming units/ml before the initial screen.

Cloning the 30 kDa CDNA. Standard methods were used to purify bacteriophage λ particle from the amplified cDNA library and to extract the recombinant DNAs (Sambrook, et al., 1989). Degenerative oligonucleotides were designed based on the amino acid sequences from peptide 23 and peptide 25 and used for primer-directed amplification of the DNA isolated from the library. Since the position of the peptides relative to each other within the protein was not known, both the coding and reverse complement sequences were synthesized. The coding and reverse complement sequences for peptide 23 used were 5'-GCN GAR CAY GGN CCN ACN TGY ATG G-3' (SEQ ID NO:9) and 5'-C CAT RCA NGT NGG NCC RTG YTC NGC-3' (SEQ ID NO:10), respectively, and for peptide 25 were 5'- AAY CAR CAR GGN TGG AA-3' (SEQ ID NO:11) and 5'-TTC CAN CCY TCY TGR TT-3' (SEQ ID NO:12), respectively. In these designations, N is inosine, R is A or G, Y is T or C. The oligonucleotides were synthesized and purified by HPLC by Midland Certified Reagent Co. (Midland, Tex.). Conditions for amplification of the DNA by the polymerase chain reaction were 20 mM Tris/Cl pH 8.4, 50 mM KCl, 2.5 mM $MgCl_2$, 0.1 mg/ml bovine serum albumin, 10 mM concentration of each dATP, dCTP, dTTP, dGTP, 50 pmol of each primer, 2.5 units Taq DNA polymerase, and 1 µg cDNA (Saiki, et al., 1988). Thirty cycles of amplification were performed at 92° C. for 1 min, 45° C. for 30 s, and 72° C. for 30 s. A specific PCR product of 400 base pairs was amplified from the isolated cDNAs and subcloned into the SmaI site of Bluescript KS⁻ (Stratagene, La Jolla, Calif.). An $[\alpha^{32}P]$-CTP-labeled riboprobe was synthesized and used to screen the cDNA library. Solution hybridization and stringent washing was performed using standard procedures (Sambrook, et al., 1989). One positive clone was plaque-purified from an initial screen of $1×10^6$ clones. The cDNA was directionally subcloned into the prokaryotic expression vector, pSPORT 1 (Life Technologies, Inc.), using the SalI and NotI cloning sites. A series of nested deletions were constructed (Erase-A-Base kit, Promega, Madison, Wis.) to generate overlapping clones from both the 5' and 3' ends of the cDNA. Both strands of the cDNA were sequenced by the dideoxynucleotide sequencing method of Sanger using the Sequenase Kit Version 2 (United States Biochemical Corp., Cleveland, Ohio) (Sanger, et al., 1977). Electrophoresis was performed in an 8% polyacrylamide gel (Hydrolink, AT Biochem, Malvern, Pa.) with 8M urea and 25% formamide (v/v). The regions sequenced are indicated in FIG. 1.

In vitro Transcription/Translation of the Cloned CDNA. NotI linearized pSPORT 1/cDNA template (2.5 µg) was transcribed in a 100 μl reaction containing 40 mM Tris/Cl (pH 7.5), 6 mM MgCl$_2$, 2 mM spermidine, 10 mM NaCl, 10 mM dithiothreitol, 100 units RNAsin, 0.5 mM of each UTP, CTP, GTP, ATP, and 40 units T7 RNA polymerase for 2 h at 37° C. In vitro translation reactions were performed in parallel and included either 15 μg of isolated mitochondria alone or mitochondria plus 4 μg of the transcribed RNA. A rabbit reticulocyte lysate kit was used following the instructions of the manufacturer (Du Pont-NEN, Boston, Mass.). The proteins were synthesized in the presence of [$^{35}$S]-methionine for 1 h at 37° C. and the reactions were frozen at -20° C. An equal volume of each reaction was analyzed by two-dimensional SDS-PAGE as described above. The gels were prepared for fluorography using Resolution (E.M. Corp., Chestnut Hill, Mass.), dried under moderate heat and vacuum, and exposed to x-ray film at -80° C.

Expression of the 30-kDa Protein in MA-10 Cells and COS 1 Cells. The full length SalI-NotI 1456 base pair 30-kDa cDNA was subcloned into the eukaryotic expression vector, pCMV (Andersson, et al., 1989). MA-10 cells were transfected with DNA by a liposome-mediated uptake using the LipofectAMINE reagent (Life Technologies, Inc., Gaithersburg, Md.) (Hawley-Nelson, et al., 1993). Plasmid DNA used in transfection experiments was purified by CsCl density gradient followed by polyethylene glycol precipitation. The DNA was mixed with 1/10 the final volume of Waymouth's media minus serum and minus antibiotics (WAY$^{--}$) and added to an equal volume of WAY$^{--}$ media containing the LipofectAMINE reagent. The DNA/lipid solution was gently mixed and incubated for 30 min at room temperature, then WAY$^{--}$ media was added to achieve the final concentration of the DNA and LipofectAMINE reagent of 5 μg/ml and 20 μg/ml respectively. The cells were washed once with WAY$^-$ media, incubated with transfection mix for 6 h, washed once with PBS, then incubated with Waymouth's plus 15% horse serum. The same procedure was used for transfection of COS 1 cells except Dulbecco's modified Eagle's media minus serum and antibiotics was used for the transfection media. For isolation of mitochondria for immunoblot analysis, cells were grown on 100-mm dishes. For progesterone production assays, MA-10 cells were plated into 96 well plates at 75,000 cells/well the day before the experiment. Typically, 8 wells each were transfected with either pCMV or pCMV+30-kDa cDNA for one experimental set.

A reporter construct expressing a tartrate-resistant acid phosphatase (TRAP) was used to determine the efficiency of transfection of MA-10 cells by the LipofectAMINE reagent. The tartrate-resistant acid phosphatase expression plasmid contains the full-length human cDNA cloned into the pcD-NAl vector provided by Dr. G. D. Roodman (Univ. of Texas HSC, San Antonio, Tex.) (Reddy, et al., 1993). Forty-eight hours post-transfection the cells were fixed directly in the wells with 2% glutaraldehyde, then stained for tartrate-resistant acid phosphatase activity using an acid phosphatase staining kit (Sigma Chemical Co., St. Louis, Mo.). Several wells of MA-10 cells were transfected with the tartrate-resistant acid phosphatase expression plasmid for each experiment and the positively stain cells were counted by visual inspection using an inverted light microscope. Typically, 5–7% of the cells were stained positive for tartrate-resistant acid phosphatase expression.

Immunoblot Analysis. Mitochondria were isolated from either MA-10 or COS 1 cells transfected with either pCMV or pCMV +30 kDa cDNA 48 hours post-transfection. For experiments in which progesterone production was measured (as described above), cells were solubilized directly in the well with 0.1% SDS, the cell homogenates were collected and combined from all 8 wells, and the protein was precipitated using trichloroacetic acid. The protein was solubilized in sample buffer (25 mM Tris/Cl, pH 6.8, 1% SDS, 5% β-mercaptoethanol, 1 mM EDTA, 4% glycerol, and 0.01% bromophenol blue) and loaded onto a 12.5% SDS-PAGE minigel (Mini-Protean II System, Bio-Rad, Richmond, Calif.). Electrophoresis was performed at 200 V for 45 min using standard SDS-PAGE buffer as described above, and the proteins were electrophoretically transferred to a polyvinylidene difluoride membrane (Bio-Rad) at 100 V for 2 h at 4° C. using the transfer buffer described above. For immunodetection of the 30 kDa protein, antipeptide antibodies were generated in rabbits against amino acids 88–98 of the 30 kDa proteins. The peptide was synthesized and the antibodies were produced in rabbits on a fee for service basis by Research Genetics (Huntsville, Ala.). The immunoblot procedure was as follows; the membrane was incubated in blocking buffer (PBS buffer containing 4% Carnation non-fat dry milk and 0.5% Tween-20) at room temperature for 1 h, then incubated in fresh blocking buffer containing the primary label (rabbit sera containing the specific antipeptide antibodies) for an additional hour at room temperature. Next, the membrane was washed with PBS containing 0.5% Tween-20, 3 times for 10 min each wash, then incubated for 1 h at room temperature with fresh blocking buffer containing the secondary antibody, donkey anti-rabbit IgG conjugated with horseradish peroxidase (Amersham Life Sciences, Arlington Heights, Ill.). The membrane was washed as before, and the specific signal was detected by chemiluminescence using the Renaissance kit from Du Pont-NEN.

Polyclonal antiserum has been generated to presequences of StAR, in particular, to a signal sequence from amino acid 10 to 26 of SEQ ID NO:2, and to a targeting sequence from amino acid 36 to 47 of SEQ ID NO:2. Antibodies of these polyclonal antisera were tested and immunoreact with precursor forms of StAR. Further polyclonal antiserum was generated to signal sequence from amino acid 1 to 26 of SEQ ID NO:2, this antiserum reacts with the signal peptide.

Radioimmunoassay. 48 hours post-transfection, the growth medium was replaced with Waymouth's minus horse serum. After 6 h at 37° C., 5% CO$_2$, progesterone was measured directly in the media by radioimmunoassay as previously described (Resko, et al., 1974). The progesterone antibody was obtained from Holly Hill Biologicals, (Hillsboro, Oreg.).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Purification of 30-kDa Proteins 1 and 2

The present example provides for the purification of the 30 kDa proteins 1 and 2. The family of LH-inducible proteins previously identified and characterized by the present inventors in mitochondria isolated from MA-10 cells represented approximately 0.2% of the total cell protein and 0.7% of the mitochondrial protein (Table 3). Due to the limited amount of the in vivo induced protein, the present inventors purified the 30 kDa proteins from the mitochondria by enriching a postmitochondrial fraction for the specific 30 kDa proteins and separating the enriched fraction by two-dimensional SDS-PAGE. The proteins were electrophoretically transferred to nitrocellulose, and the specific 30 kDa proteins were isolated by excising the nitrocellulose spot containing the bound protein. The purification scheme developed to isolate the 30 kDa proteins is summarized under "Materials and Methods" hereinabove. The objective was to isolate a sufficient amount of the 30 kDa protein for in situ tryptic digestion, peptide separation, and microsequence analysis.

Proteolytic digestion of each of the 30 kDa forms produced identical peptides, indicating that the difference in these four forms is due to post-translational modifications of a single protein. The present inventors had previously shown that the difference in the isoelectric points for forms 3 and 4 is due to phosphorylation of forms 1 and 2. The 30 kDa mitochondrial proteins are processed from a larger precursor protein synthesized in response to hormone stimulation of MA-10 cells. However, the precursor protein has a short half-life and is difficult to detect in MA-10 cells (Stocco and Sodeman, 1991; Epstein and Orme-Johnson, 1991). For this reason the present inventors focused on the purification of the 30 kDa proteins which are stable in mitochondria isolated from MA-10 cells. These proteins had been detected by metabolically labeling MA-10 cells in vivo with [$^{35}$S]-methionine/cysteine and isolating the mitochondria for two dimensional SDS-PAGE analysis followed by fluorography.

The present inventors first determined if the quantity of the 30 kDa proteins in isolated mitochondria was sufficient to detect by protein staining. The 30 kDa proteins were readily detectable by silver-stain after two dimensional SDS PAGE of mitochondria isolated from Bt$_2$cAMP-stimulated MA-10 cells. As expected, the proteins were absent in unstimulated cells. The major difficulty in the purification of the 30 kDa proteins from MA-10 cells was the lack of a bioassay, therefore, each step of the purification was monitored by silver-stained two dimensional SDS PAGE analysis of the proteins.

Table 3 summarizes the enrichment and recovery of the 30 kDa proteins.

TABLE 3

Purification of the 30-kDa Proteins from Bt$_2$cAMP-stimulated MA-10 Cells[1]

| Fraction | Total protein % recovery | μg 30-kDa proteins/ mg sample protein | Enrichment of the 30-kDa proteins-fold enrichment | % recovery 30-kDa proteins |
|---|---|---|---|---|
| Mitochondria | 100 | 7 | 1 | 100 |
| Mitoplasts | 56 ± 10 | ND[a] | ND | ND |
| CHAPS-soluble | 22 ± 6 | 18 | 2.6 | 55 |
| 30-kDa fraction n = 16 | 0.6 ± 0.3 | 94 ± 28 | 13 | 7 |

[a]Shown are the results from the purification of the 30-kDa proteins from 40–50 mg of mitochondria. Each fraction was separated by two dimensional-gel electrophoresis and the proteins were visualized by silver stain. 1 gel was analyzed for the mitochondrial fraction, 2 gels with different protein concentrations for the CHAPS-soluble fraction, and 4 gels with varying protein concentrations for the 30-kDa fraction were run simultaneously and stained for protein. The silver-stained image was captured, and the integrated intensity (II) of each spot (protein) was estimated using a Bioimage visage 2000 (Millipore). The percent of the total integrated intensity of each spot/protein was automatically determined. To estimate the amount of 30-kDa protein, the percent of total II for the 30kDa protein spots were multiplied by the amount of total protein loaded onto the first dimension gel. The results are shown as micrograms 30-kDa protein (sum of 1–4) per mg of fraction sample.
[a]ND, mitoplast fraction not determined.

The purification achieved a 13-fold enrichment with a 7% recovery of the 30 kDa proteins. The goal was to sufficiently enrich the 30 kDa proteins in a final fraction in order to resolve a sufficient quantity (1–2 μg) of the specific 30 kDa proteins by 2D SDS-PAGE. The 1D preparative gel enriched the 30 kDa proteins to approximately 100 μg/mg of the final 30 kDa fraction which allowed the present inventors to isolate the 30 kDa protein. The 30 kDa fraction was treated with alkaline phosphatase just prior to 2D SDS-PAGE to concentrate the 30 kDa proteins into forms 1 and 2 (Stocco and Clark, 1993). Comparison of the protein profiles for the 30 kDa fraction purified from mitochondria isolated from control and Bt$_2$cAMP-stimulated MA-10 cells was used to verify that the correct protein spots, 30 kDa 1 and 2, were isolated. Using this purification, approximately 75 mg of isolated mitochondria was required to isolate approximately 200 pmol of the 30 kDa proteins from Bt$_2$cAMP-stimulated MA-10 cells. Quantitatively, 60% of the total 30 kDa proteins was recovered in 30 kDa 2, and 40% was recovered in 30 kDa 1. The difference between form 1 and form 2 may be that of methylation, acetylation, sulfation, prenylation, or myristylation, and the like.

EXAMPLE 2

Cloning the cDNA and Analysis of the Encoded 30 kDa Protein

The present example provides for the cloning and sequence analysis of the cDNA encoding the 30 kDa protein, and analysis of the protein sequence. Even though 30 kDa 1 and 30 kDa 2 were thought to be identical proteins, they were isolated and stored separately. To ensure one homogeneous protein was used for microsequence analysis, only the 30 kDa protein 2 was sent to the Harvard Microchemical Facility where in situ digestion, tryptic peptide separation, and microsequence analysis was performed on a fee-for-service basis. Three tryptic peptides, #23, #25, and #45, were selected for microsequence analysis. The amino acid sequences for the peptides were determined to be:

Peptide 23: AEHGPTCMVLHPLA, (SEQ ID NO:3)
Peptide 25: ALGILNNQEGWK, (SEQ ID NO:4)
Peptide 45: GSTCVLAGMATHFGEMPEQ, (SEQ ID NO:5)

The GenEMBL and SWISS-PROT data bases were searched for similarities to the three peptide sequences and no significant homologies were found (Fasta and TFasta programs, GCG Package, University of Wisconsin, Madison Wis.).

A cDNA library was constructed using polyA+ RNA purified from total RNA that was isolated from $Bt_2cAMP$-stimulated MA-10 cells as described hereinabove. Using the amino acid sequences of the 3 peptides, degenerative oligonucleotides 17–24 bases in length were synthesized and used to amplify the 30 kDa cDNA from the cDNA library by the polymerase chain reaction (PCR)(Saiki et al., 1988). A 400 bp specific PCR product was amplified using a combination of the peptide 25 coding and peptide 23 reverse complement oligonucleotides. The PCR generated DNA was used to probe the cDNA library and a 1456 bp full-length clone was isolated. Both strands of the cDNA were sequenced and a partial restriction map was generated. Also included are the positions of the PCR amplified sequence, the initiating ATG codon, and the termination TAA codon. SEQ ID. NO:1 shows the nucleotide sequence of the 30 kDa cDNA which contains an open reading frame of 852 base pairs that encodes a protein of 284 amino acids with a calculated molecular weight of 31.6 kDa. The deduced amino acid sequence for the 30 kDa protein is shown by three letter code under the nucleic acid sequence. The three peptide sequences derived from the protein microsequence analysis are encoded in the cDNA which confirmed the translation reading frame.

Although the predicted molecular weight based on the deduced amino acid sequence is lower than the observed size of the mitochondrial precursor protein by 2D SDS-PAGE, inspection of the amino terminal amino acid sequence for the deduced protein revealed characteristics consistent with mitochondrial targeting sequences (von Heijne, 1986; von Heijne et al., 1989). Namely, the first 25 amino acids lack acidic amino acids, are enriched in Arg (12%), Ser (8%), Ala (8%), and Leu (12%), and the predicted secondary structure is an amphipathic alpha helix. In addition, the amino acids at positions 38, 40, and 43 are Arg, Leu, and Ser, respectively, which would fit the amino acid consensus cleavage site, R-X-Φ-X-X-S, where X represents any amino acid and Φ represents a hydrophobic residue (Hendrick, et al., 1989). This amino acid motif is highly conserved in mitochondrial presequences that undergo a 2 step sequential cleavage of mitochondrial precursors by the matrix processing protease (MPP) and the mitochondrial intermediate processing peptide (MIP) (Kalousek, et al., 1988; Kiebler et al., 1993). No significant similarities were found to the cDNA sequence when the GenEMBL and SWISS-PROT data bases were searched.

The signal sequence is represented by amino acids at positions 1 to about 26 of SEQ ID NO:2, more particularly, from about amino acids at positions 10 to 26 of SEQ ID NO:2. The targeting sequence is represented by amino acids at about positions 36 to 47 of SEQ ID NO:2. The mature 30 kDa protein has methionine at position 48 as the N-terminal amino acid.

To confirm that the cDNA clone encodes the precursor and mature mitochondrial proteins, the cDNA was transcribed in vitro and the synthesized RNA was used in an in vitro translation reaction. A two dimensional SDS-PAGE of the [$^{35}$S]-methionine labeled in vitro translated proteins in the presence of mitochondria demonstrated that the mobility of the proteins was identical to the LH-induced newly synthesized proteins in MA-10 cells which were previously identified as the 37 kDa precursor protein and the 30 kDa mitochondrial proteins. Therefore, the cDNA obtained based on the amino acid sequence data for the 30 kDa 2 protein encodes all forms of the previously described family of mitochondrial proteins.

EXAMPLE 3

Improved Production of Progesterone and StAR protein by Recombinant Means; Induction of Steroidogenesis The present example demonstrates that the expression of the 37 kDa protein has an effect on steroid production in mammalian cells.

MA-10 cells were transfected with the 30 kDa cDNA and progesterone production was measured as follows. The full-length cDNA was subcloned into the pCMV eukaryotic expression vector and transfected into MA-10 cells using LipofectAMINE (Life Technologies, Inc.). Cells (75,000 per well) were plated in a 96 well plate the day before transfection. The cells were incubated with the DNA/lipid transfection mixture for 6 hours, washed one time with PBS, and then incubated in Waymouths+15% horse serum. Forty-eight hours post-transfection the cells were washed with PBS and Waymouths media (minus serum) was placed back onto the cells. After 6 h, the medium was removed and progesterone was measured by radioimmunoassay. The cells were lysed directly in the wells with 0.1% SDS and protein was determined by the method of Bradford (1976). Progesterone production is shown in Table 4 as picograms progesterone produced per mg protein per 6 h. The transfected cells were not treated with hormone and progesterone was measured directly in the media after a 6 h incubation. A significant increase in progesterone production was observed in MA-10 cells transfected with the 30 kDa cDNA compared to cells transfected with the pCMV vector alone (Table 4). Expression of the 30 kDa protein resulted in a 1.5 to 3.7 fold increase in steroidogenesis with an average rate of 166 pg progesterone produced per mg protein per hour.

TABLE 4

Progesterone production in MA-10 cells transiently transfected with the 30kDa cDNA[1]

| Study[2] | n | Control (nontransfected) | pCMV pg progesterone/mg protein/6 h | pCMV + cDNA | pCMV + cDNA/ pCMV- fold increase[2] |
|---|---|---|---|---|---|
| I | 3 | ND[3] | 361 ± 38 | 1239 ± 347 | 3.4 |
| II | 4 | ND | 317 ± 77 | 519 ± 42 | 1.6 |
| III | 8 | ND | 403 ± 145 | 1775 ± 444 | 3.7 |
| IV | 8 | 756 ± 135 | 787 ± 174 | 1148 ± 174 | 1.5 |
| V | 8 | 469 ± 58 | 428 ± 81 | 1378 ± 233 | 3.2 |
| VI | 8 | 779 ± 171 | 1071 ± 143 | 3146 ± 768 | 2.9 |

[1]Control (non-transfected) cells were grown in WAY+ for 48 h and washed once with PBS+ before WAY– media was added; PCMV, MA-10 cells were transfected with the pCMV vector alone; pCMV + cDNA, MA-10 cells were transfected with the pCMV + 30kDa cDNA. n represents the number of wells transfected for each experiment. The progesterone was measured in each well and the mean ± the standard deviation is shown for each study. The Student's t test was used to determine the statistical difference between the pCMV and pCMV + 30kDa cDNA samples.
[2]In every study, the difference was significant with a p value < 0.01.
[3]ND, not determined.

The level of expression of the 30 kDa protein in the transfected MA-10 cells was determined by immunoblot analysis. Antibodies having binding specificity for amino acids 88–98 of the 30 kDa proteins (see Materials and Methods) recognized a protein at approximately 30 kDa only in mitochondria isolated from Bt$_2$cAMP-stimulated MA-10 cells while no immunodetectable protein was observed in the non-stimulated cells. In addition, the antibody recognized all four 30-kDa protein spots specifically when mitochondrial proteins from stimulated MA-10 cells were resolved by two-dimensional SDS-PAGE. Cell homogenates of the MA-10 cells that had been transfected with pCMV+30 kDa cDNA and used for progesterone production for expression of the 30 kDa protein were tested, however, no immunodetectable protein was observed. Since the pCMV vector does not replicate in MA-10 cells, and only 5% of the cells are transfected with plasmid DNA based upon expression of the tartrate-resistant acid reporter protein, it was not surprising that the protein could not be detected in cell homogenates collected from approximately 1×10$^6$ cells (8 wells from a 96 well plate).

In order to verify that the cDNA was being expressed in eukaryotic cells, COS 1 cells were used to transfect the PCMV+30 kDa cDNA since the PCMV plasmid can be replicated in these cells and approximately 80% of the cells are transfected with plasmid DNA based on the expression of reporter protein. Forty-eight hours post-transfection, mitochondria were isolated and the 30 kDa protein expression was determined by immunoblot analysis. An immunospecific protein of approximately 30 kDa was readily detectable in isolated mitochondria only from COS 1 cells that had been transfected with the 30 kDa cDNA, indicating the cDNA does express the same protein as the Bt$_2$cAMP-stimulated MA-10 cells. In addition, a 36.5 kDa protein was detected in the COS 1 cells which would be consistent with the precursor protein. Importantly, the 30 kDa protein was also detectable in MA-10 cells transfected with pCMV+30 kDa cDNA by immunoblot analysis when isolated mitochondria were analyzed. The level of expression of the 30 kDa protein in the transfected MA-10 cells was approximately 7% of that observed in the Bt$_2$cAMP-stimulated MA-10 cells. Thus, these data indicate that the expression of the 30 kDa protein is sufficient to induce steroid production in MA-10 cells in the absence of hormone stimulation.

The present inventors have named this protein the Steroidogenic Acute Regulatory protein, StAR. While not wishing to be bound by any particular theory regarding a mechanism of action, the following working model for the acute regulation of steroidogenesis in Leydig cells by StAR is provided. The precursor protein is rapidly synthesized in the cytosol in response to hormone stimulation. The precursor binds to a receptor on the mitochondrial membrane and processing begins. Processing consists of the N-terminus entering the mitochondrial matrix and being cleaved to the 30 kDa form. It is during the processing that contact sites between the inner and outer mitochondrial membranes form and this very hydrophobic environment provides the medium through which cholesterol may pass to the inner membrane Thus, it may be the processing of StAR from a 37 kDa form to a 30 kDa form that is functionally active in the transport of cholesterol and results in increased steroid production. It is also possible this protein may bind cholesterol.

EXAMPLE 4

Expression of StAR Precursor Protein in *E. coli*

The present example describes studies carried out to express the 37 kDa precursor StAR protein in *E. coli* for overproduction thereof.

The *E. coli* expression vector, pKK233-2, (Clontech, Palo Alto, Calif.) contains an IPTG-inducible promoter (P$_{trc}$), a LacZ ribosome binding site, and a unique Nco1 cloning site that provides an ATG initiation codon. Since expression of mitochondrial proteins tends to be toxic to bacterial host cells, basal levels of expression can be greatly reduced in *E. coli* strains that overproduce the lac repressor (lacI$^q$) and optimal expression can be achieved by induction for a short period of time.

StAR cDNA was cloned in pSPORT vector (GIBCO Life Technologies, Gaithersburg, Md.) and this vector was used for PCR amplification of the coding sequence for StAR. Primers were designed to introduce restriction sites (Nco1 at the 5' end and HindIII at the 3' end) for directional subcloning into the pKK233-2 vector. Ligation of the amplified StAR cDNA fragments with the pKK233-2 vector constructed a recombinant pKK233-2/StAR plasmid. The *E. coli* strains, JM109 and DH5αF'IQ, were transformed with this plasmid and maintained in LB media (10 g tryptone, 5 g yeast extract, 10 g NaCl, and 100 μg/ml ampicillin). For expression, a fresh culture (15–30 ml LB media) inoculated with the transformed *E. coli* was grown to an OD$_{600}$=0.6 at 37° C., then IPTG (isopropyl β-D-thiogalactopyranoside) was added to a final concentration of 1 mM. Protein expression was induced at 30° C. for 2 hours and cells were harvested. Cells were lysed by sonication in buffer containing 50 mM Tris (pH 8.0), 150 mM NaCl, 0.02% sodium azide, 0.1% SDS, 1% NP-40, 0.5% sodium deoxycholate, 100 μg/ml phenylmethylsulfonyl fluoride, 2 μg/ml aprotinin, and 2 μg/ml leupeptin.

From staining patterns on gels, it is apparent that significant amounts of StAR protein were made. The extract of *E. coli* DH5αF'IQ with the StAR cDNA insert contained a 37 kDa polypeptide which was approximately 3% of the total cellular protein. This 37 kDa protein was not detected in *E. coli* without the plasmid. The protein reacted with the antibody raised against amino acids 88–98 of StAR.

For isolation and purification of the StAR precursor protein, the sonic lysate was ultracentrifuged (100,000×g, 1 h), and the supernatant passed through an affinity column packed with Protein A agarose beads crosslinked with the anti-StAR antibody having binding specificity for amino acids 88–98 of StAR. The fractions enriched for StAR precursor protein were concentrated and further purified by passage through a gel filtration column (packed with Sephadex G-75 beads). Flow-through fractions were tested for the StAR precursor protein by Western blot analysis and the purity was assayed using a silver staining method.

EXAMPLE 5

StAR is Hormonally Regulated and Developmentally Regulated

The present example provides studies that show that the production of StAR protein is hormonally regulated, as well as developmentally regulated in vivo.

MA-10 cells were stimulated with Bt$_2$cAMP and StAR mRNA levels were determined by Northern blot analysis. Within 1 hour of Bt$_2$cAMP stimulation, two major transcripts of approximately 3400 nt and 1600 nt, and one minor transcript of 2700 nt, were detected. StAR mRNAs were markedly induced (20×) after 2 hours of hormone stimulation with maximal levels obtained after 6 hours. Subsequent to the marked mRNA induction, the greatest induction (10×) in StAR protein was detected after 4 hours of Bt$_2$cAMP stimulation by immunoblot analysis. Comparatively lower levels of StAR could be detected after 1 hour of hormone stimulation with maximal levels accumulated within 8 hours. Hormone-induced progesterone production rose above basal levels in MA-10 cells typically within 1 hour with the greatest increase in rate of steroid output measured between 2–4 hours of hormone stimulation, consistent with the induction in StAR protein. These data indicate that StAR is transcriptionally regulated by a cAMP-mediated mechanism. Immunoblot analysis of several mouse tissues indicates that StAR protein is expressed in the adrenal, ovary, and testis, and is not expressed in brain, muscle, liver, spleen, heart or placenta. The developmental expression of StAR was assessed by in situ hybridization analysis of mouse embryonic tissue. Earliest detection of StAR transcripts was at embryonic day 10.5 (E10.5) in the genital ridge. By E12.5–E14.5, StAR was readily detected in the interstitial cells of the testis and adrenal cortex and continued to be expressed in the adult. StAR expression was absent in the ovary at E12.5–E14.5, but was abundant in the adult ovary. The developmental pattern of expression for StAR parallels that observed previously for cytochrome P450scc which provides further supporting evidence for the importance of StAR in steroid hormone biosynthesis.

The present inventors have generated stable transfected MA-10 cell lines that constitutively synthesize the 30 kDa protein and that produce steroid constitutively at a level several fold higher (about 9×) than basal parental MA-10 cells.

EXAMPLE 6

Screening for Mutations in the StAR Gene for Identifying Steroid Hormone-Dependent Pathologies The present example provides methods by which the nucleic acid molecules, in particular, fragments of the nucleotide sequence of SEQ ID NO:1 may be used to detect mutations within the StAR gene. These screening techniques may be used to identify a number of different pathologies; particularly steroid hormone-dependent pathologies, such as, for example, lipoid congenital adrenal hyperplasia (LCAH), adrenal hypoplasia congenita, hypogonadotropic hypogonadism, precocious puberty, or McCune-Albright syndrome.

The identification of highly conserved mutations and the development of an appropriate screen would provide regulations and standards for clinical testing and screening for these metabolic disorders.

StAR DNA may be used for screening adrenal tissue obtained from patients with Lipoid Congenital Adrenal Hyperplasia (LCAH) to test for a possible role of StAR in the disease state. This can be achieved with Southern blotting and hybridization with a cDNA probe. Fairly large DNA rearrangements of greater than 500 bp may be detected in this manner. However, it may be that the mutations within the StAR gene resulting in steroid hormone-dependent pathologies are too small to detect by Southern blotting. This would be the case if they are due to point mutations or to small insertions, deletions or other rearrangements.

Smaller StAR gene mutations are detected by DNA sequencing which can be performed on a genomic DNA template, a cDNA template prepared from RNA by reverse transcriptase, or on a PCR product. In an attempt to detect mutations rapidly, several methods are available; chemical cleavage, denaturing gradient electrophoresis (DGGE) and ribonuclease cleavage, and single strand conformation polymorphism. These methods and others may be used in conjunction with the present invention and may be performed after PCR amplification of the DNA region under study.

EXAMPLE 7

Gene Therapy

This prophetic example describes some of the ways in which the present invention may be of use in the treatment of steroid hormone-dependent disorders, especially those characterized as involving defects in cholesterol transport.

A wild-type human StAR gene may be introduced into human tissue to provide a wild-type copy of the gene and therefore, also a wild-type protein product, that may correct the genetic lesion that causes the steroid hormone-dependent disorder.

Human adenovirus or retrovirus are means for introducing genes into tissue. Adenoviruses are double-stranded DNA tumor viruses with genome sizes of approximate 36 kb. As a model system for eukaryotic gene expression, adenoviruses have been widely studied and well characterized, and have already been used in a gene transfer system (see e.g., WO9506743, WO9502697, WO9500655, WO9428938, WO9419478, and WO9412649, each publication is incorporated by reference herein) . This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

In general, adenovirus gene transfer systems are based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers. Persistent expression of transgenes follows adenoviral infection.

Particular advantages of an adenovirus system for delivering foreign genes and their protein products to a cell include (i) the ability to substitute relatively large pieces of viral DNA with foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible.

Patients testing positive for LCAH and for whom the medical indication for adenovirus-mediated gene transfer has been established, would be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

Recombinant adenovirus providing the wild-type StAR gene may be prepared and purified by any of a variety of methods, so as to provide a preparation suitable for administration to human subjects, including, but not limited to cesium chloride density gradient centrifugation, and subsequently tested for efficacy and purity. Virus is administered to patients by means of intravenous administration in any pharmacologically acceptable solution, either as a bolus or as an infusion over a period of time. Generally speaking, it is believed that the effective number of functional virus particles to be administered would range from $5 \times 10^{10}$ to $5 \times 10^{12}$.

Patients would remain hospitalized for at least 48 hr to monitor acute and delayed adverse reactions. Serum levels of a protein product may be monitored or Southern blots may be performed to follow the efficacy of the gene transfer. Adjustments to the treatment may include adenovirus constructs that use different promoters or a change in the number of pfu injected.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alberta et al., (1989) *J. Biol. Chem.* 264, 2368–2372.
Almahbobi, et al., (1992) *Exp. Cell Res.* 200, 361–369.
Andersson, et al., (1989) *J. Biol. Chem.* 264, 8222–8229.
Ardail, et al., (1991) *J. Biol. Chem.* 266, 7978–7981.
Ascoli, M. (1981) *Endocrinology* 108, 88–95.
Bonner and Laskey, (1974) *Eur. J. Biochem.* 46, 83–88.
Bradford, M. (1976)*Anal. Biochem.* 72, 248–254.
Brown, et al., (1992) *Mol. Cell. Endrocrinol.* 83, 1–9.
Camacho, et al., *J. Clin. Endocrinol. Metab.* 28:153–161, 1968.
Caracciolo et al. (1989) *Science*, 245:1107.
Chanderbhan, et al., (1982) *J. Biol. Chem.* 257, 8928–8934.
Chomczynski and Sacchi, (1987) *Anal. Biochem.* 162, 156–159.
Clark and Waterman, (1991)*J. Biol. Chem.* 266, 5898–5904.
Cooke, et al., (1975) *Biochem. J.* 150, 413–418.
Crivello and Jefcoate, (1980) *J. Biol. Chem.* 255, 8144–8151.
Davis and Garren, (1968) *J. Biol. Chem.* 243, 5153–5157.
Degenhart, et al., *Acta Endocrinologia* 71:512–518, 1972.
Deutscher, (1990) *Methods in Enzymology*, 182, Guide to Protein Purification, Academic Press, Inc.
Elliott, et al., (1993) *Endocrinology* 133, 1669–1677.
Epstein and Orme-Johnson, (1991) *J. Biol. Chem.* 266, 19739–19745.
Ferguson, (1963) *J. Biol. Chem.* 238, 2754–2759.
Freeman, (1987) *J.Biol. Chem.* 262, 13061–13068.
Garnier, et al., (1993) *Endocrinology* 132, 444–458.
Garren, et al., (1965) *Biochemistry* 53, 1443–1450.
Glick, et al., (1991) *Trends Cell Biol.* 1, 99–103.
Green and Orme-Johnson, (1991) *J. Steroid Biochem. Molec. Biol.* 40, 421–429.
Hall and Almahbobi, (1992) *J. Steroid Biochem. Molec. Biol.* 43, 769–777.
Hartl, F-U. (1986) *Cell* 47, 939–951.
Hauffa, et al., *Clin. Endocrinol.* 23:481–493, 1985.
Hawley-Nelson, et al., (1993) *Focus* 15, 73–79.
Haynes, et al., (1959) *J. Biol. Chem.* 234, 1421–1423.
Hendrick, et al., (1989) *Proc. Natl. Acad. Sci. U.S.A.*, 86, 4056–4060.
Jefcoate, et al., (1987) *J. Steroid Biochem.* 27, 721–729.
Jefcoate, et al., (1986) *Endocr. Res.* 12, 315–350.
Jefcoate, et al., (1992) *J. Steroid Biochem. Molec. Biol* 43, 751–767.
Jefcoate, et al., (1974) *Eur. J. Biochem.* 42, 539–551.
Kalousek, et al. (1988) *Proc. Natl. Acad. Sci U.S.A.* 85, 7536–7540.
Karaboyas and Koritz, (1965) *Biochemistry* 4, 462–468.
Kiebler, et al., (1993) *J. Memb. Biol.* 135, 191–207.
Koizumi et al., *Clin. Chim. Acta* 77:301–306, 1977.
Krueger and Orme-Johnson, (1983) *J. Biol. Chem.* 258, 10159–10167.
Laemmli, U.K. (1970) *Nature* 227, 680–688.
Lin et al., *J. Clin. Invest.* 88:1955–1962, 1991
Mendelson, et al., (1975) *Biochim. Biophys. Acta* 411, 222–230.
McEnery, et al., (1992) *Proc. Natl. Acad. Sci. U.S.A.*, 89, 3170–3174.
Merrifield, R., *J. Am. Chem. Soc.*, 85:2149, 1963.
Mertz and Pedersen, (1989) *Endocr. Res.* 15, 101–115.
O'Farrell, P.H. (1975) *J. Biol. Chem.* 250, 4007–4021.
Pedersen and Brownie, (1983) *Proc. Natl. Acad. Sci U.S.A.* 80, 1882–1886.
Pedersen and Brownie, (1987) *Science* 236, 188–190.
Pon et al., (1986) *J. Biol. Chem.* 261, 13309–13316.
Pon et al., (1986) *Endocr. Res.* 12, 429–446.
Privalle, et al., (1983) *Proc.Natl. Acad. Sci. U.S.A.* 80, 702–706.
Python, et al., (1993) *Endocrinology* 132, 1489–1496.
Reddy, et al., (1993) *BioTechniques* 15, 444–448.
Remington: The Science and Practice of Pharmacy, 19th edition, Volumes 1 and 2, A. R. Gennaro, ed., Mack Publishing Co. Easton, Pa., 1995.
Resko, et al. (1974) *Endocrinology* 94, 128–135.
Sambrook, et al., (1989) *Molecular Cloning, A Laboratory Manual*, 2nd Ed., Cold Springs Harbor Laboratory, Cold Springs Harbor, N.Y.
Saiki, et al., (1988) *Science* 239, 487–494.
Sala, et al., (1979) *J. Biol. Chem.* 254, 3861–3865.
Sanger, et al., (1977) *Proc. Natl. Acad. Sci. U.S.A.* 74,5463–5467.
Schleyer and Neupert, (1985) *Cell* 43, 339–350.
Schwaiger, et al., (1987) *J. Cell Biol.* 105, 235–246.
Simbeni, et al., (1990) *J. Biol. Chem.* 265, 281–285.
Simbeni, et al., (1991) *J. Biol. Chem.* 266, 10047–10049.
Simpson, et al., (1972) *Eur. J. Biochem.* 28, 442–450.
Stocco and Kilgore, (1988) *Biochem. J.* 249, 95–103.
Stocco and Chaudhary, (1990) *Cell. Signal.* 2, 161–170.
Stocco and Chen, (1991) *Endocrinology* 128, 1918–1926.
Stocco and Sodeman, (1991) *J. Biol. Chem.* 266, 19731–19738.
Stocco, D. M. (1992) *J. Steroid Biochem. Molec. Biol.* 43, 319–333.
Stocco and Ascoli, (1993) *Endocrinology* 132, 959–967.
Stocco, et al., (1993) *Endocrinology* 133, 2827–2832.
Stocco and Clark, (1993)*J. Steroid Biochem. Mole. Biol.* 46, 337–347.

Stone and Hechter, (1954) *Arch. Biochem. Biophysics* 51, 457–469.
Towbin, et al., (1979) *Proc. Natl. Acad. Sci. U.S.A.* 76, 4350–4354.
van Amerongen, et al., (1989) *Biochim. Biophys. Acta.* 1004, 36–43.
von Heijne, G. (1986) *EMBO J.* 5, 1335–1342.
von Heijne, et al., (1989) *Eur. J. Biochem.* 180, 535–545.

What is claimed is:

1. A purified nucleic acid molecule having a nucleotide sequence encoding a steroidogenic acute regulatory protein, the protein having a sequence having 70% to 99% identity to SEQ ID NO: 2.

2. A purified nucleic acid molecule which is the full complement and of the same length as the nucleic acid molecule of claim 1.

3. The purified nucleic acid molecule of claim 1 wherein the steroidogenic acute regulatory protein has the amino acid sequence of SEQ ID NO: 2.

4. The purified nucleic acid molecule of claim 1 further defined as having 70% to 99% identity to a nucleotide sequence of SEQ ID NO:1.

5. The purified nucleic acid molecule of claim 1 further defined as a DNA molecule and being substantially free of DNA molecules not encoding a steroidogenic acute regulatory protein.

6. A recombinant vector comprising the purified nucleic acid molecule of claim 1.

7. The recombinant vector of claim 6, further defined as an expression vector comprising a promoter operatively linked to said nucleic acid molecule.

8. The recombinant vector of claim 6, further defined as a pCMV, adenoviral, retroviral, pUC, SV40, yeast plasmid, Baculovirus or Vaccinia virus vector.

9. A recombinant host cell comprising the recombinant vector of claim 6.

10. The recombinant host cell of claim 9, further defined as a Leydig cell, a COS cell, an adrenalcortical cell, an ovarian granulosa cell, Saccharomyces cerevisiae, or Escherichia coli cell.

11. A purified nucleic acid molecule having a nucleotide sequence that encodes an amino acid sequence extending from amino acid methionine at position 48 through amino acid cysteine at position 284 of SEQ ID NO:2.

12. A purified nucleic acid molecule having a 17, 20, 25, 30, 50, 100, 200, 500, or 1000 nucleotide sequence that corresponds to, or is capable of hybridizing to the nucleic acid sequence of SEQ ID NO:1 under conditions standard for hybridization fidelity and stability.

13. A purified nucleic acid molecule having a nucleotide sequence of SEQ ID NO:9.

14. A purified nucleic acid molecule having a nucleotide sequence encoding a steroidogenic acute regulatory protein, the protein having an amino acid sequence of SEQ ID NO: 2, said nucleic acid molecule obtained by a process of:

preparing oligonucleotides that encode a segment of an amino acid sequence of SEQ ID NO:2 and that have at least 17 nucleotides;

screening an animal cell DNA library with said oligonucleotides; and obtaining the purified nucleic acid molecule having a nucleotide sequence encoding a steroidogenic acute regulatory protein, the protein having an amino acid sequence of SEQ ID NO:2.

15. A purified nucleic acid molecule having a nucleotide sequence of SEQ ID NO: 14.

16. A purified nucleic acid molecule having a nucleic acid sequence of SEQ ID NO: 10.

17. A purified nucleic acid molecule consisting of a nucleic acid sequence of SEQ ID NO: 11.

18. A purified nucleic acid molecule consisting of a nucleic acid sequence of SEQ ID NO: 12.

19. A purified nucleic acid molecule having a nucleic acid sequence of SEQ ID NO: 13.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1466 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:1:

```
GTCGACCCAC  GCGTCCGCTC  AGGACCTTGA  AAGGCTCAGG  AAGAACAACC  CTTGAGCACC     60
TCAGCACTCA  GCATGTTCCT  CGCTACGTTC  AAGCTGTGTG  CTGGAAGCTC  CTATAGACAT    120
ATGCGGAATA  TGAAAGGATT  AAGGCACCAA  GCTGTGCTGG  CCATTGGCCA  AGAGCTCAAC    180
TGGAGAGCAC  TGGGGGATTC  CAGTCCCGGG  TGGATGGGTC  AAGTTCGACG  TCGGAGCTCT    240
CTGCTTGGTT  CTCAACTGGA  AGCAACACTC  TATAGTGACC  AGGAGCTGTC  CTACATCCAG    300
CAGGGAGAGG  TGGCTATGCA  GAAGGCCTTG  GGCATACTCA  ACAACCAGGA  AGGCTGGAAG    360
AAGGAAAGCC  AGCAGGAGAA  CGGGGACGAA  GTGCTAAGTA  AGATGGTGCC  AGATGTGGGC    420
AAGGTGTTTC  GCTTGGAGGT  GGTGGTAGAC  CAGCCCATGG  ACAGACTCTA  TGAAGAACTT    480
GTGGACCGCA  TGGAGGCCAT  GGGAGAGTGG  AACCCAAATG  TCAAGGAGAT  CAAGGTCCTG    540
CAGAGGATTG  GAAAAGACAC  GGTCATCACT  CATGAGCTGG  CTGCGGCGGC  AGCAGGCAAC    600
CTGGTGGGGC  CTCGAGACTT  CGTGAGCGTG  CGCTGTACCA  AGCGCAGAGG  TTCCACCTGT    660
GTGCTGGCAG  GCATGGCCAC  ACATTTTGGG  GAGATGCCGG  AGCAGAGTGG  TGTCATCAGA    720
GCTGAACACG  GCCCCACCTG  CATGGTGCTT  CATCCACTGG  CTGGAAGTCC  CTCCAAGACT    780
AAACTCACTT  GGCTGCTCAG  TATTGACCTG  AAGGGGTGGC  TGCCGAAGAC  AATCATCAAC    840
CAGGTCCTAT  CGCAGACCCA  GATAGAGTTC  GCCAACCACC  TGCGCAAGCG  CCTGGAAGCC    900
AGCCCTGCCT  CTGAGGCCCA  GTGTTAAGGA  CTGTCCACCA  CATTGACCTG  CAAATCATTG    960
GAAGCTCTCA  CAGGAAGCCT  GCAAGTCTGT  CCATCTTCAG  CTAACAGCAT  CGGGAGGGGT   1020
GGTAGTCAGG  AGACACTAGG  ACTGACTGGT  AAAATCAGGA  TCAGCAAAAT  AGAAATGAGG   1080
CTTAGAATAA  AAGTTCTCTA  GTGTCTCCCA  CTGCATAGCT  GTGAAGGCTA  AGGGATAAGT   1140
AGCTATGAAA  CCTTTCATCT  AGGCTTGTAT  ATGCTGACCT  AAAAGACACC  AGCAGCTACG   1200
AACAGGGGAT  GCTAAGGATC  GGGAACTGTT  GTCTTACCAG  CTCCAAATGT  CACTACCTGA   1260
AGGCAGTGTG  CACACAAAGC  AAGGTCTTGC  CTAGGAAACT  CTGTAAAAGT  TCTCCTCTGT   1320
AAAAGGCCAG  AACTTGAATG  AAACTACCTA  CAAAGGGCCT  TTCCAGAGTA  TTCCAACTTT   1380
TCTCTGAGGA  GAAATGAAAC  CATCATTGTG  CCGACTTCCC  TACTAATCCC  ATGACAATAA   1440
AGAACATACA  TAAAAAAAAA  AAAAAA                                           1466
```

( 2 ) INFORMATION FOR SEQ ID NO:2:

(i) SEQUENCE CHARACTERISTICS:
    (A) LENGTH: 284 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:2:

| Met | Phe | Leu | Ala | Thr | Phe | Lys | Leu | Cys | Ala | Gly | Ser | Ser | Tyr | Arg | His |
|---|---|---|---|---|---|---|---|---|---|---|---|---|---|---|---|
| 1 | | | | 5 | | | | | 10 | | | | | 15 | |

| Met | Arg | Asn | Met | Lys | Gly | Leu | Arg | His | Gln | Ala | Val | Leu | Ala | Ile | Gly |
|---|---|---|---|---|---|---|---|---|---|---|---|---|---|---|---|
| | | | 20 | | | | | 25 | | | | | 30 | | |

| Gln | Glu | Leu | Asn | Trp | Arg | Ala | Leu | Gly | Asp | Ser | Ser | Pro | Gly | Trp | Met |
|---|---|---|---|---|---|---|---|---|---|---|---|---|---|---|---|
| | | 35 | | | | | 40 | | | | | 45 | | | |

| Gly | Gln | Val | Arg | Arg | Arg | Ser | Ser | Leu | Leu | Gly | Ser | Gln | Leu | Glu | Ala |
|---|---|---|---|---|---|---|---|---|---|---|---|---|---|---|---|
| | 50 | | | | | 55 | | | | | 60 | | | | |

| Thr | Leu | Tyr | Ser | Asp | Gln | Glu | Leu | Ser | Tyr | Ile | Gln | Gln | Gly | Glu | Val |
|---|---|---|---|---|---|---|---|---|---|---|---|---|---|---|---|
| 65 | | | | | 70 | | | | | 75 | | | | | 80 |

| Ala | Met | Gln | Lys | Ala | Leu | Gly | Ile | Leu | Asn | Asn | Gln | Glu | Gly | Trp | Lys |
|---|---|---|---|---|---|---|---|---|---|---|---|---|---|---|---|
| | | | | 85 | | | | | 90 | | | | | 95 | |

| Lys | Glu | Ser | Gln | Gln | Glu | Asn | Gly | Asp | Glu | Val | Leu | Ser | Lys | Met | Val |
|---|---|---|---|---|---|---|---|---|---|---|---|---|---|---|---|
| | | | 100 | | | | | 105 | | | | | 110 | | |

| Pro | Asp | Val | Gly | Lys | Val | Phe | Arg | Leu | Glu | Val | Val | Val | Asp | Gln | Pro |
|---|---|---|---|---|---|---|---|---|---|---|---|---|---|---|---|
| | | | 115 | | | | | 120 | | | | | 125 | | |

| Met | Asp | Arg | Leu | Tyr | Glu | Glu | Leu | Val | Asp | Arg | Met | Glu | Ala | Met | Gly |
|---|---|---|---|---|---|---|---|---|---|---|---|---|---|---|---|
| | 130 | | | | | 135 | | | | | 140 | | | | |

| Glu | Trp | Asn | Pro | Asn | Val | Lys | Glu | Ile | Lys | Val | Leu | Gln | Arg | Ile | Gly |
|---|---|---|---|---|---|---|---|---|---|---|---|---|---|---|---|
| 145 | | | | | 150 | | | | | 155 | | | | | 160 |

| Lys | Asp | Thr | Val | Ile | Thr | His | Glu | Leu | Ala | Ala | Ala | Ala | Ala | Gly | Asn |
|---|---|---|---|---|---|---|---|---|---|---|---|---|---|---|---|
| | | | | 165 | | | | | 170 | | | | | 175 | |

| Leu | Val | Gly | Pro | Arg | Asp | Phe | Val | Ser | Val | Arg | Cys | Thr | Lys | Arg | Arg |
|---|---|---|---|---|---|---|---|---|---|---|---|---|---|---|---|
| | | | 180 | | | | | 185 | | | | | 190 | | |

| Gly | Ser | Thr | Cys | Val | Leu | Ala | Gly | Met | Ala | Thr | His | Phe | Gly | Glu | Met |
|---|---|---|---|---|---|---|---|---|---|---|---|---|---|---|---|
| | | 195 | | | | | 200 | | | | | 205 | | | |

| Pro | Glu | Gln | Ser | Gly | Val | Ile | Arg | Ala | Glu | His | Gly | Pro | Thr | Cys | Met |
|---|---|---|---|---|---|---|---|---|---|---|---|---|---|---|---|
| | 210 | | | | | 215 | | | | | 220 | | | | |

| Val | Leu | His | Pro | Leu | Ala | Gly | Ser | Pro | Ser | Lys | Thr | Lys | Leu | Thr | Trp |
|---|---|---|---|---|---|---|---|---|---|---|---|---|---|---|---|
| 225 | | | | | 230 | | | | | 235 | | | | | 240 |

| Leu | Leu | Ser | Ile | Asp | Leu | Lys | Gly | Trp | Leu | Pro | Lys | Thr | Ile | Ile | Asn |
|---|---|---|---|---|---|---|---|---|---|---|---|---|---|---|---|
| | | | | 245 | | | | | 250 | | | | | 255 | |

| Gln | Val | Leu | Ser | Gln | Thr | Gln | Ile | Glu | Phe | Ala | Asn | His | Leu | Arg | Lys |
|---|---|---|---|---|---|---|---|---|---|---|---|---|---|---|---|
| | | | 260 | | | | | 265 | | | | | 270 | | |

| Arg | Leu | Glu | Ala | Ser | Pro | Ala | Ser | Glu | Ala | Gln | Cys | | | | |
|---|---|---|---|---|---|---|---|---|---|---|---|---|---|---|---|
| | | 275 | | | 280 | | | | | | | | | | |

(2) INFORMATION FOR SEQ ID NO:3:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

| Ala | Glu | His | Gly | Pro | Thr | Cys | Met | Val | Leu | His | Pro | Leu | Ala |
|---|---|---|---|---|---|---|---|---|---|---|---|---|---|
| 1 | | | | 5 | | | | | 10 | | | | |

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ala  Leu  Gly  Ile  Leu  Asn  Asn  Gln  Glu  Gly  Trp  Lys
1                  5                        10
```

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Gly  Ser  Thr  Cys  Val  Leu  Ala  Gly  Met  Ala  Thr  His  Phe  Gly  Glu  Met
1                  5                        10                       15
Pro  Glu  Gln
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Asn  Gln  Glu  Gly  Trp  Lys
1                  5
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ala  Glu  His  Gly  Pro  Thr  Cys  Met  Val
1                  5
```

( 2 ) INFORMATION FOR SEQ ID NO:8:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Ile  Leu  Asn  Asn  Gln  Glu  Gly  Trp  Lys  Lys  Glu
```

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: modified_base
        (B) LOCATION: one-of(3, 12, 15, 18)
        (D) OTHER INFORMATION: /mod_base=OTHER
            / note= "N = (A or C or G or T/U) or (unknown or other)"

(ix) FEATURE:
        (A) NAME/KEY: modified_base
        (B) LOCATION: 6
        (D) OTHER INFORMATION: /mod_base=OTHER
            / note= "R = A or G"

(ix) FEATURE:
        (A) NAME/KEY: modified_base
        (B) LOCATION: one-of(9, 21)
        (D) OTHER INFORMATION: /mod_base=OTHER
            / note= "Y = C or T/U"

(xi) SEQUENCE DESCRIPTION: SEQ ID NO:9:

GCNGARCA Y G GNCCNACNTG Y ATGG    25

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: modified_base
        (B) LOCATION: one-of(5, 17)
        (D) OTHER INFORMATION: /mod_base=OTHER
            / note= "R = A or G"

(ix) FEATURE:
        (A) NAME/KEY: modified_base
        (B) LOCATION: one-of(8, 11, 14, 23)
        (D) OTHER INFORMATION: /mod_base=OTHER
            / note= "N = (A or C or G or T/U) or (unknown or other)"

(ix) FEATURE:
        (A) NAME/KEY: modified_base
        (B) LOCATION: 20
        (D) OTHER INFORMATION: /mod_base=OTHER
            / note= "Y = C or T/U"

(xi) SEQUENCE DESCRIPTION: SEQ ID NO:10:

CCATRCANGT NGGNCCRTG Y TCNGC    25

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid ( A ) DESCRIPTION: /desc = "DNA"

( i x ) FEATURE:
  ( A ) NAME/KEY: modified_base
  ( B ) LOCATION: 3
  ( D ) OTHER INFORMATION: /mod_base=OTHER
    / note= "Y = C or T/U"

( i x ) FEATURE:
  ( A ) NAME/KEY: modified_base
  ( B ) LOCATION: one-of(6, 9)
  ( D ) OTHER INFORMATION: /mod_base=OTHER
    / note= "R = A or G"

( i x ) FEATURE:
  ( A ) NAME/KEY: modified_base
  ( B ) LOCATION: 12
  ( D ) OTHER INFORMATION: /mod_base=OTHER
    / note= "N = (A or C or G or T/U) or (unknown or other)"

( x i ) SEQUENCE DESCRIPTION: SEQ ID NO:11:

AA Y CAR CARG  GNTGGAA                                                                17

( 2 ) INFORMATION FOR SEQ ID NO:12:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:12:

TTCCANCC Y T  C Y TGRTT                                                               17

( 2 ) INFORMATION FOR SEQ ID NO:13:

( i ) SEQUENCE CHARACTERISTICS:
    ( A ) LENGTH: 401 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:13:

| AACCAGGAAG | GCTGGAAGAA | GGAAAGCCAG | CAGGAGAACG | GGGACGAAGT | GCTAAGTAAG | 60 |
|---|---|---|---|---|---|---|
| ATGGTGCCAG | ATGTGGGCAA | GGTGTTTCGC | TTGGAGGTGG | TGGTAGACCA | GCCCATGGAC | 120 |
| AGACTCTATG | AAGAACTTGT | GGACCGCATG | GAGGCCATGG | GAGAGTGGAA | CCCAAATGTC | 180 |
| AAGGAGATCA | AGGTCCTGCA | GAGGATTGGA | AAAGACACGG | TCATCACTCA | TGAGCTGGCT | 240 |
| GCGGCGGCAG | CAGGCAACCT | GGTGGGGCCT | CGAGACTTCG | TGAGCGTGCG | CTGTACCAAG | 300 |
| CGCAGAGGTT | CCACCTGTGT | GCTGGCAGGC | ATGGCCACAC | ATTTTGGGGA | GATGCCGGAG | 360 |
| CAGAGTGGTG | TCATCAGAGC | TGAACACGGC | CCCACCTGCA | T | | 401 |

( 2 ) INFORMATION FOR SEQ ID NO:14:

( i ) SEQUENCE CHARACTERISTICS:
    ( A ) LENGTH: 1466 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "RNA"

( x i ) SEQUENCE DESCRIPTION: SEQ ID NO:14:

| | | | | | | |
|---|---|---|---|---|---|---|
| GUCGACCCAC | GCGUCCGCUC | AGGACCUUGA | AAGGCUCAGG | AAGAACAACC | CUUGAGCACC | 60 |
| UCAGCACUCA | GCAUGUUCCU | CGCUACGUUC | AAGCUGUGUG | CUGGAAGCUC | CUAUAGACAU | 120 |
| AUGCGGAAUA | UGAAAGGAUU | AAGGCACCAA | GCUGUGCUGG | CCAUUGGCCA | AGAGCUCAAC | 180 |
| UGGAGAGCAC | UGGGGGAUUC | CAGUCCCGGG | UGGAUGGGUC | AAGUUCGACG | UCGGAGCUCU | 240 |
| CUGCUUGGUU | CUCAACUGGA | AGCAACACUC | UAUAGUGACC | AGGAGCUGUC | CUACAUCCAG | 300 |
| CAGGGAGAGG | UGGCUAUGCA | GAAGGCCUUG | GGCAUACUCA | ACAACCAGGA | AGGCUGGAAG | 360 |
| AAGGAAAGCC | AGCAGGAGAA | CGGGGACGAA | GUGCUAAGUA | AGAUGGUGCC | AGAUGUGGGC | 420 |
| AAGGUGUUUC | GCUUGGAGGU | GGUGGUAGAC | CAGCCCAUGG | ACAGACUCUA | UGAAGAACUU | 480 |
| GUGGACCGCA | UGGAGGCCAU | GGGAGAGUGG | AACCCAAAUG | UCAAGGAGAU | CAAGGUCCUG | 540 |
| CAGAGGAUUG | GAAAAGACAC | GGUCAUCACU | CAUGAGCUGG | CUGCGGCGGC | AGCAGGCAAC | 600 |
| CUGGUGGGGC | CUCGAGACUU | CGUGAGCGUG | CGCUGUACCA | AGCGCAGAGG | UUCCACCUGU | 660 |
| GUGCUGGCAG | GCAUGGCCAC | ACAUUUUGGG | GAGAUGCCGG | AGCAGAGUGG | UGUCAUCAGA | 720 |
| GCUGAACACG | GCCCCACCUG | CAUGGUGCUU | CAUCCACUGG | CUGGAAGUCC | CUCCAAGACU | 780 |
| AAACUCACUU | GGCUGCUCAG | UAUUGACCUG | AAGGGUGGC | UGCCGAAGAC | AAUCAUCAAC | 840 |
| CAGGUCCUAU | CGCAGACCCA | GAUAGAGUUC | GCCAACCACC | UGCGCAAGCG | CCUGGAAGCC | 900 |
| AGCCCUGCCU | CUGAGGCCCA | GUGUUAAGGA | CUGUCCACCA | CAUUGACCUG | CAAAUCAUUG | 960 |
| GAAGCUCUCA | CAGGAAGCCU | GCAAGUCUGU | CCAUCUUCAG | CUAACAGCAU | CGGGAGGGU | 1020 |
| GGUAGUCAGG | AGACACUAGG | ACUGACUGGU | AAAAUCAGGA | UCAGCAAAAU | AGAAAUGAGG | 1080 |
| CUUAGAAUAA | AAGUUCUCUA | GUGUCUCCCA | CUGCAUAGCU | GUGAAGGCUA | AGGGAUAAGU | 1140 |
| AGCUAUGAAA | CCUUUCAUCU | AGGCUUGUAU | AUGCUGACCU | AAAAGACACC | AGCAGCUACG | 1200 |
| AACAGGGGAU | GCUAAGGAUC | GGGAACUGUU | GUCUUACCAG | CUCCAAAUGU | CACUACCUGA | 1260 |
| AGGCAGUGUG | CACACAAAGC | AAGGUCUUGC | CUAGGAAACU | CUGUAAAAGU | UCUCCUCUGU | 1320 |
| AAAAGGCCAG | AACUUGAAUG | AAACUACCUA | CAAAGGGCCU | UUCCAGAGUA | UUCCAACUUU | 1380 |
| UCUCUGAGGA | GAAAUGAAAC | CAUCAUUGUG | CCGACUUCCC | UACUAAUCCC | AUGACAAUAA | 1440 |
| AGAACAUACA | UAAAAAAAAA | AAAAAA | | | | 1466 |